(12) United States Patent
Lesieur et al.

(10) Patent No.: US 6,605,632 B1
(45) Date of Patent: Aug. 12, 2003

(54) SUBSTITUTED CYCLIC COMPOUNDS, PREPARATION METHOD AND PHARMACEUTICAL COMPOSITIONS CONTAINING THEM

(75) Inventors: Daniel Lesieur, Gondecourt (FR); Frédérique Klupsch, Hulluch (FR); Gérald Guillaumet, Saint Jean le Blanc (FR); Marie-Claude Viaud, Tours (FR); Michel Langlois, Sceaux (FR); Caroline Bennejean, Charenton le Pont (FR); Pierre Renard, Le Chesnay (FR); Philippe Delagrange, Issy les Moulineaux (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/700,056

(22) PCT Filed: May 10, 1999

(86) PCT No.: PCT/FR99/01101
§ 371 (c)(1),
(2), (4) Date: Nov. 10, 2000

(87) PCT Pub. No.: WO99/58496
PCT Pub. Date: Nov. 18, 1999

(30) Foreign Application Priority Data

May 12, 1998 (FR) .................................. 98 05957

(51) Int. Cl.[7] ................... C07D 307/85; C07D 333/64; A61K 31/34; A61K 31/36; A61P 5/02
(52) U.S. Cl. ................ 514/411; 514/412; 514/443; 514/444; 514/452; 514/454; 548/427; 548/429; 548/430; 548/452; 548/490; 549/32; 549/33; 549/44; 549/46; 549/48; 549/49; 549/52; 549/433; 549/458; 549/462; 549/463; 549/464
(58) Field of Search ................ 548/427, 429, 548/430, 452, 490; 549/32, 33, 44, 46, 48, 49, 52, 433, 458, 462, 464, 463; 514/411, 412, 443, 444, 454, 450

(56) References Cited

U.S. PATENT DOCUMENTS 4,663,347 A * 5/1987 Atkinson et al. ........... 549/468
5,773,467 A * 6/1998 Dyke et al. ................ 549/468
5,863,936 A * 1/1999 Gaeta et al. ................ 549/51

OTHER PUBLICATIONS

Drugs of the Future 2000, 25(9), pp 945–957.
Cagnacci et al., J. Pineal Res., 1997, 22, pp 16–19.
Life Sciences 2000, 66(6) pp 503–509.
Bylesjö E.I. et al., International Journal of Eating Disorders, 1996, 20(4), pp 443–446.
Ferrari E. et al., Biol, Phychiatry, 1990, 27, pp 1007–1020.
Brown G.M., CNS Drugs, 1995 3(3), pp 209–226.
Psychopharmacology 1990, 100: 222–226.
Brain Research 1990, 528m 170–174.
Schizophrenia Research 1992, 7, 77–84.
Journal of Affective Disorders 1987, 12 203–206.
Medical Hypotheses 1988, 27, 271–276.
Behavioural Pharmacology 1999, 10, 73083.
Neuropharmacology 2000, 39, 1865–71.
Exp. Brain Res.1995, 107, 321–325.
Endocrinology 1999, vol. 140(2), 1009–1012.
Medical Hypotheses 1991, 34, pp 300–309.
Current Pharmaceutical Design 2001, 7, 909–931.
Science 1985, 227, pp 714–720.
Rec. Med, Vet. 1991, 167(3/4), pp 227–239.
Drug Development Research 1996, 39, pp 167–173.
Am. J. Physiol. 1998, 275, pp 139–144.
Leone M. et al., Cephalalgia, 1996, 16, pp 494–496.
Cephalalgia, 1995, 15, pp 136–139.
Shui–Wang Ying et al., Eur. Journal of Pharmacology, 1993, 246, pp 89–96.
Laudon M. et al., Journal of clinical Endocrinology and Metabolism, 1996, 8194, pp 1336–1342.
Lissoni P., British Journal of Cancer 1996, 74, pp 1466–1468.

* cited by examiner

*Primary Examiner*—Richard L. Raymond
*Assistant Examiner*—Venkataraman Balasubrasubramanian
(74) *Attorney, Agent, or Firm*—The Firm of Hueschen and Sage

(57) ABSTRACT

The invention concerns compounds of formula (I): R—A—R' wherein: A is as defined in the description; R represents a group (V), (VI), (VII) or (VIII), where E, Q, $R^1$, $R^2$, $R^3$, v and $R^4$ are as defined in the description; R' represents a —$(CH_2)_t$—$R^5$ group wherein t and $R^5$ are as defined in the description

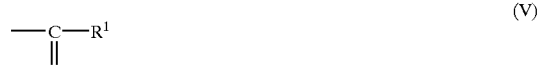

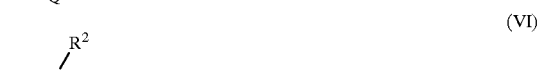

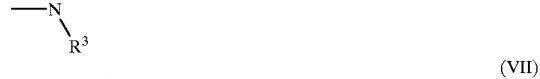

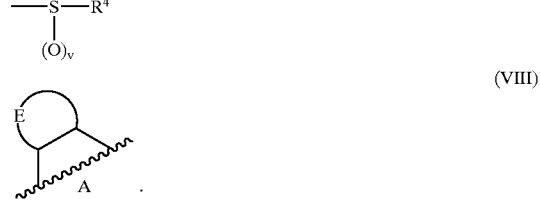

41 Claims, No Drawings

SUBSTITUTED CYCLIC COMPOUNDS, PREPARATION METHOD AND PHARMACEUTICAL COMPOSITIONS CONTAINING THEM

FIELD OF THE INVENTION

The present invention relates to new substituted cyclic compounds having very valuable pharmacological characteristics in respect of melatoninergic receptors.

DESCRIPTION OF THE PRIOR ART

The prior art discloses retroamide chain indoles substituted by amides or carbamates for use as antagonists of GnRH (WO 9721707) and amide chain indoles substituted by amides, carbamates or ureas for use as antihypertensive agents (U.S. Pat. No. 4,803,218).

Retroamide chain benzofuran and benzothiophene compounds substituted by amides or carbamates have also been described as anti-inflammatory agents (EP 685475) or inhibitors of bone resorption.

BACKGROUND OF THE INVENTION

In the last ten years, numerous studies have demonstrated the major role played by melatonin (5-methoxy-N-acetyltryptamine) in numerous physiopathological phenomena and also in the control of circadian rhythm. Its half-life is, however, quite short owing to its being rapidly metabolised. It is thus very useful to be able to provide the clinician with melatonin analogues that are metabolically more stable and that have an agonist or antagonist character on the basis of which a therapeutic effect that is superior to that of the hormone itself may be expected. In addition to their beneficial action on disorders of circadian rhythm (J. Neurosurg. 1985, 63, pp 321–341) and sleep disorders (Psychopharmacology, 1990, 100, pp 222–226), ligands of the melatoninergic system have valuable pharmacological properties in respect of the central nervous system, especially anxiolytic and antipsychotic properties (Neuropharmacology of Pineal Secretions, 1990, 8 (3–4), pp 264–272) and analgesic properties (Pharmacopsychiat., 1987, 20, pp 222–223), and also for the treatment of Parkinson's disease (J. Neurosurg. 1985, 63, pp 321–341) and Alzheimer's disease (Brain Research, 1990, 528, pp 170–174). Those compounds have also shown activity on certain cancers (Melatonin—Clinical Perspectives, Oxford University Press, 1988, pp 164–165), ovulation (Science 1987, 227, pp 714–720), diabetes (Clinical Endocrinology, 1986, 24, pp 359–364), and in the treatment of obesity (International Journal of Eating Disorders, 1996, 20 (4), pp 443–446). Those various effects take place via the intermediary of specific melatonin receptors. Molecular biology studies have shown the existence of a number of receptor sub-types that can bind the hormone (Trends Pharmacol. Sci., 1995, 16, p 50; WO 97.04094). It has been possible to locate some of those receptors and to characterise them for different species, including mammals. In order to be able to understand the physiological functions of those receptors better, it is very valuable to have specific ligands available. Moreover, by interacting selectively with one or other of those receptors, such compounds can be excellent medicaments for the clinician in the treatment of pathologies associated with the melatoninergic system, some of which have been mentioned above.

In addition to the fact that the compounds of the present invention are new, they exhibit very great affinity for melatonin receptors and/or selectivity for one or other of the melatoninergic receptor sub-types.

DETAILED DESCRIPTION OF THE INVENTION

More specifically, the present invention relates to compounds of formula (I):

$$R—A—R' \qquad (I)$$

wherein
A represents:
a ring system of formula (II):

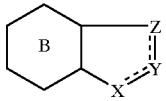

(II)

wherein
X represents an oxygen, sulphur or nitrogen atom or a group $C(H)_q$ (wherein q is 0, 1 or 2) or $NR_0$ (wherein $R_0$ represents a hydrogen atom, a linear or branched $(C_1-C_6)$alkyl group, an aryl group, an aryl-$(C_1-C_6)$alkyl group in which the alkyl moiety is linear or branched, or $SO_2Ph$),
Y represents a nitrogen atom or a group $C(H)_q$ (wherein q is 0, 1 or 2),
Z represents a nitrogen atom or a group $C(H)_q$ (wherein q is 0, 1 or 2), but X, Y and Z cannot represent three hetero atoms simultaneously,
B represents a benzene or pyridine nucleus,
the symbol ⋯ means that the bonds may be single or double, it being understood that the valency of the atoms is respected, wherein R substitutes the ring B and R' substitutes the ring containing the groups X, Y and Z, or R and R' substitute the ring B,
a ring system of formula (III):

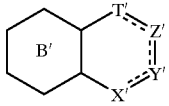

(III)

wherein
X' represents an oxygen or sulphur atom or a group $C(H)_q$ (wherein q is 0, 1 or 2),
Y' represents a group $C(H)_q$ (wherein q is 0, 1 or 2) or $NR_0$ wherein $R_0$ is as defined hereinbefore,
Z' represents a group $C(H)_q$ (wherein q is 0, 1 or 2) or $NR_0$ wherein $R_0$ is as defined hereinbefore,
T' represents an oxygen or sulphur atom or a group $C(H)_q$ (wherein q is 0, 1 or 2),
it being understood that, when Y' or Z' represents a hetero atom, the other three variables ((X', Z', T') and (X', Y', T'), respectively) cannot represent a hetero atom,
the symbol ⋯ is as defined hereinbefore,
B' represents:
a benzene nucleus,
a naphthalene nucleus when X', Y', Z' and T' do not simultaneously represent a group $C(H)_q$ (wherein q is 0, 1 or 2),
or a pyridine nucleus when X' and T' simultaneously represent a group $C(H)_q$ (wherein q is 0, 1 or 2), wherein R substitutes the ring B' and R' substitutes the ring containing the groups X', Y', Z' and T', or R and R' substitute the ring B', a ring system of formula (IV):

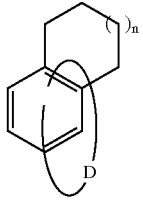
(IV)

representing the ring systems (IV$_{a-d}$):

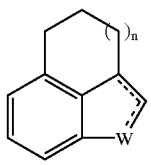
(IV$_a$)

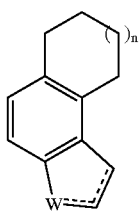
(IV$_b$)

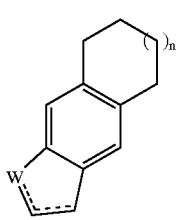
(IV$_c$)

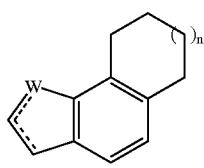
(IV$_d$)

wherein n is an integer such that $0 \leq n \leq 3$,

W represents an oxygen, sulphur or nitrogen atom, or a group $[C(H)_q]_p$ (wherein q is 0, 1 or 2, and p is 1 or 2) or $NR_0$ wherein $R_0$ is as defined hereinbefore, the symbol ... is as defined hereinbefore, wherein R' substitutes the ring

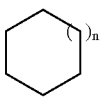

and R substitutes one or other of the two other rings, or a biphenyl group wherein R substitutes one of the benzene rings and R' substitutes the other, or R and R' substitute the same benzene ring, it being understood that the ring systems of formulae (II), (III) and (IV) and the biphenyl group may be unsubstituted or substituted (in addition to the substituents R and R') by from 1 to 6 radicals, which may be the same or different, selected from $R_a$, $OR_a$, $COR_a$, $COOR_a$, $OCOR_a$, $OSO_2CF_3$ and halogen atoms, wherein $R_a$ represents a hydrogen atom, an unsubstituted or substituted linear or branched ($C_1$–$C_6$)alkyl group, an unsubstituted or substituted linear or branched ($C_2$–$C_6$)alkenyl group, an unsubstituted or substituted linear or branched ($C_2$–$C_6$)alkynyl group, a linear or branched ($C_1$–$C_6$)polyhaloalkyl group, an unsubstituted or substituted ($C_3$–$C_8$)cycloalkyl group, an unsubstituted or substituted ($C_3$–$C_8$) cycloalkyl-($C_1$–$C_6$)alkyl group in which the alkyl group is linear or branched, an unsubstituted or substituted ($C_3$–$C_8$)cycloalkenyl group, an unsubstituted or substituted ($C_3$–$C_8$) cycloalkenyl-($C_1$–$C_6$)alkyl group in which the alkyl group is linear or branched, an aryl group, an aryl-($C_1$–$C_6$)alkyl group in which the alkyl moiety is linear or branched, an aryl-($C_1$–$C_6$)alkenyl group in which the alkenyl moiety is linear or branched, a heteroaryl group, a heteroaryl-($C_1$–$C_6$)alkyl group in which the alkyl moiety is linear or branched, a heteroaryl-($C_1$–$C_6$)alkenyl group in which the alkenyl moiety is linear or branched, an unsubstituted or substituted linear or branched ($C_1$–$C_6$)heterocycloalkyl group, an unsubstituted or substituted heterocycloalkenyl group, a substituted or unsubstituted heterocycloalkyl-($C_1$–$C_6$)alkyl group in which the alkyl moiety is linear or branched, or a substituted or unsubstituted heterocycloalkenyl-($C_1$–$C_6$) alkyl group in which the alkyl moiety is linear or branched, R represents:

a group of formula (V):

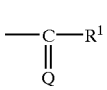
(V)

wherein

Q represents a sulphur or oxygen atom, $R^1$ represents a group $NR'_a R''_a$ or $OR^1_a$ (wherein $R'_a$ and $R''_a$, which may be the same or different, may take any of the values of $R_a$ and may also form, together with the nitrogen atom carrying them, a 5- to 10-membered cyclic group which may contain, in addition to the nitrogen atom by which it is linked, from one to three hetero atoms selected from oxygen, sulphur and nitrogen, and $R^1_a$ may take any of the values of $R_a$ except for the hydrogen atom), a group of formula (VI):

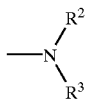
(VI)

wherein
$R^2$ represents a group $R_a$ as defined hereinbefore,
$R^3$ represents a group $COR'_a$, $CSR'_a$, $CONR'_aR''_a$, $CSNR'_aR''_a$, $COOR'_a$, $CSOR'_a$ or $S(O)_vR'_a$ (wherein $R'_a$ and $R''_a$, which may be the same or different, are as defined hereinbefore and may also form, together with the nitrogen atom carrying them, a cyclic group as defined hereinbefore, and v is 1 or 2), a group of formula (VII):

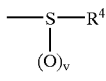
(VII)

wherein v is as defined hereinbefore and $R^4$ represents a group $NR'_aR''_a$, $NR_aCOR'_a$, $NR_aCSR'_a$, $NR_aCONR'_aR''_a$, $NR_aCSNR'_aR''_a$ or $NR_aCOOR'_a$, wherein $R_a$, $R'_a$ and $R''_a$ are as defined hereinbefore, or, when A represents a ring system of formula (II) or (III) or a biphenyl group, forms, together with two adjacent carbon atoms of the ring structure A carrying it, a ring of formula (VIII):

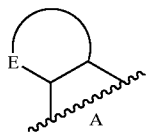
(VIII)

wherein E represents a group

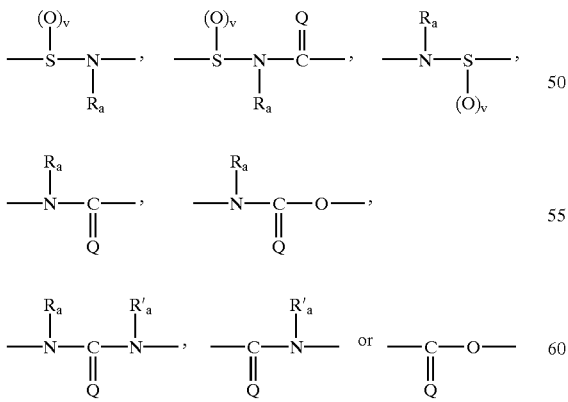

wherein r, Q, $R_a$, $R'_a$ and v are as defined hereinbefore, the ring formed containing from 5 to 7 atoms and it being possible for the ring to contain from 1 to 3 hetero atoms selected from nitrogen, sulphur and oxygen, and one or more as unsaturations, and being optionally substituted by one or more radicals, which may be the same or different, selected from $R_a$, $OR_a$, $COR_a$, $COOR_a$, $OCOR_a$, $NR'_aR''_a$, $NR_aCOR'_a$, $CONR'_aR''_a$, cyano, oxo, $SR_a$, $S(O)R_a$, $SO_2R_a$, $CSR_a$, $NR_aCSR'_a$, $CSNR'_aR''_a$, $NR_aCONR'_aR''_a$, $NR_aCSNR'_aR''_a$ and halogen atoms, herein $R_a$, $R'_a$ and $R''_a$, which may be the same or different, are as defined hereinbefore and $R'_a$ and $R''_a$ may also form, together with the nitrogen atom carrying them, a cyclic group as defined hereinbefore, and R' represents a group of formula (IX):

(IX)

wherein
G represents an alkylene chain $-(CH_2)_t-$ (wherein t is an integer such that $0 \leq t \leq 4$ when A represents a tricyclic structure and such that $1 \leq t \leq 4$ when A represents a bicyclic structure), optionally substituted by one or more radicals, which may be the same or different, selected from $R_a$, $OR_a$, $COOR_a$, $COR_a$ (in which $R_a$ is as defined hereinbefore) or halogen atoms, and $R^5$ represents a group

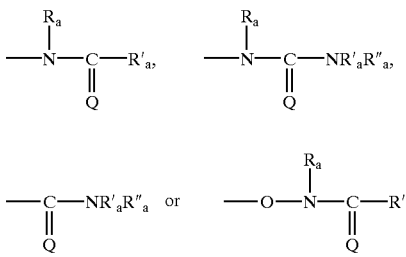

wherein Q, $R_a$, $R'_a$ and $R''_a$ (which may be the same or different) are as defined hereinbefore, it being possible for $R'_a$ and $R''_a$ to form, together with the nitrogen atom carrying them, a cyclic group as defined hereinbefore, it being understood that:
"heterocycloalkyl" is taken to mean any saturated mono- or poly-cyclic group containing from 5 to 10 atoms containing from 1 to 3 hetero atoms selected from nitrogen, oxygen and sulphur, "heterocycloalkenyl" is taken to mean any non-aromatic mono- or poly-cyclic group containing one or more unsaturations, containing from 5 to 10 atoms and which may contain from 1 to 3 hetero atoms selected from nitrogen, oxygen and sulphur, the term "substituted" used in respect of the expressions "alkyl", "alkenyl" and "alkynyl" indicates that the groups in question are substituted by one or more radicals, which may be the same or different, selected from hydroxy, linear or branched ($C_1$–$C_6$)alkoxy, linear or branched ($C_1$–$C_6$)alkyl, linear or branched ($C_1$–$C_6$) polyhaloalkyl, amino and halogen atoms, the term "substituted" used in respect of the expressions "cycloalkyl", "cycloalkylalkyl", "cycloalkenyl", "cycloalkenylalkyl", "heterocycloalkyl", "heterocycloalkenyl", "heterocycloalkylalkyl" and "heterocycloalkenylalkyl" indicates that the cyclic moiety of the groups in question is substituted by one or more radicals, which may be the same or different, selected from hydroxy, linear or branched ($C_1$–$C_6$) alkoxy, linear or branched ($C_1$–$C_6$)alkyl, linear or branched ($C_1$–$C_6$)polyhaloalkyl, amino and halogen atoms, "aryl" is taken to mean any aromatic, mono- or poly-cyclic group containing from 6 to 22 carbon atoms, and also the biphenyl group, "heteroaryl" is taken to mean any aromatic mono- or poly-cyclic group containing from 5 to 10 atoms containing from 1 to 3 hetero atoms selected from nitrogen, oxygen and sulphur, it being possible for the "aryl" and "heteroaryl" groups to be substituted by one or more radicals, which may be the same or different, selected from hydroxy, linear or branched ($C_1$–$C_6$)alkoxy, linear or branched ($C_1$–$C_6$) alkyl, linear or branched ($C_1$–$C_6$)polyhaloalkyl, cyano, carboxy, nitro, amino and halogen atoms, to it being understood that:

when A represents an indole nucleus, there cannot be any substituents in the 2-position, when A represents an indole nucleus and R represents a group —NHCOR'$_a$, —NHCOOR'$_a$ or NHCONR'$_a$R"$_a$, then G—$R^5$ cannot represent a group —(CH$_2$)$_2$—NHCOR$_b$ wherein R$_b$ represents a ($C_1$–$C_4$)alkyl or CF$_3$ group, when A represents a benzofuran or benzothiophene nucleus, there cannot be any COPh groups (wherein Ph is substituted or unsubstituted) in the 2-position, when A represents a benzofuran or benzothiophene nucleus, R cannot represent a group —NR$_a$COR$_c$, —NHSO$_2$R$_c$, —NHCOCH$_2$R$_c$, or NHCONHR$_c$ wherein R$_c$ represents a heterocyclic or aryl group, when A represents a tetrahydronaphthalene group, $R^5$ cannot represent a group CONR'$_a$R"$_a$, when A represents a hydrocarbon ring system and $R^5$ represents a group NHCOR'$_a$, then R cannot represent a group COOR'$_a$, the compound of formula (I) cannot represent:
  N-{8-[(acetylamino)methyl]-2-naphthyl}-2-methylpropanamide,
  N-(2-{5-[(4-ethoxyanilino)sulphonyl]-1H-indol-3-yl}ethyl)acetamide,
  8-[(acetylamino)methyl]-N-isopropyl-2-naphthamide, their enantiomers and diastereoisomers, and addition salts thereof with a pharmaceutically acceptable acid or base.

Among the pharmaceutically acceptable acids there may mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid etc.

Among the pharmaceutically acceptable bases there may mentioned, without implying any limitation, sodium hydroxide, potassium hydroxide, triethylamine, tert-butylamine etc.

Preferred compounds of the invention are those wherein A represents a ring system of formula (II'):

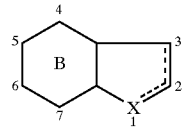
(II')

wherein B, X and symbol ... are as defined hereinbefore, or (III'):

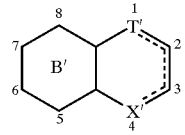

wherein B wherein B', T', X' and the symbol ... are as defined hereinbefore.

The invention advantageously relates to compounds wherein A (unsubstituted or substituted by a single substituent (in addition to R and R') preferably in the 2-position (formula II') or in the 3-position (formula III'), represents a cyclic system of formula (II'):

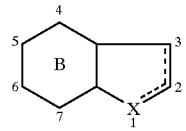

wherein B, X and the symbol ... are as defined hereinbefore, such as, for example, (dihydro)benzothiophene, (dihydro)benzofuran, indole, indoline, indan, indene, azaindole, thienopyridine or furopyridine, or of formula (III'):

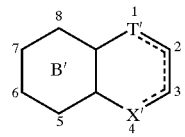

wherein B', T', X' and the symbol ... are as defined hereinbefore, such as, for example, naphthalene, tetrahydronaphthalene, (thio)chroman, (dihydro) benzodioxin, (dihydro)benzoxathiin, (dihydro) benzochromene.

Even more advantageously, the invention relates to compounds wherein A of formula (II') or (III') is substituted by R in the 5-position (formula II')or 7-position (formula III') and by R' in the 3-position (formula II') or 1- or 2-position (formula III').

Preferred substituents R of the invention are those represented by a group of formula (V), (VI) or (VII).

More advantageously, preferred substituents R of the invention are those represented by a group of formula (V) wherein Q represents an oxygen atom and $R^1$ represents a group NR'$_a$R"$_a$ (wherein R'$_a$ and R"$_a$ are as defined hereinbefore) or OR$^1_a$ (wherein R$^1_a$ is as defined hereinbefore), a group of formula (VI) wherein $R^3$ represents a group COR'$_a$ or COOR'$_a$ (wherein R'$_a$ is as defined hereinbefore), or a group of formula (VII) wherein v is 2 and $R^4$ represents a group NR'$_a$R"$_a$ as defined hereinbefore.

Even more advantageously, preferred substituents R of the invention are those represented by a group CONR'$_a$R"$_a$ or SO$_2$NR'$_a$R"$_a$ wherein R'$_a$ and R"$_a$, which may be the same or different, represent a hydrogen atom or an alkyl, polyhaloalkyl, alkenyl, alkynyl, cycloalkyl, cycloalkenyl, cycloalkylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl, or form, together with the nitrogen atom carrying them, a piperazine, piperidine, morpholine or thiomorpholine group, or by a group NCOR'$_a$, NCOOR'$_a$ or COOR$^1_a$ wherein R'$_a$ represents a hydrogen atom, an alkyl, polyhaloalkyl, alkenyl, alkynyl, cycloalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl, and R$^1_a$ represents an alkyl, polyhaloalkyl, alkenyl, alkynyl, cycloalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl.

Preferred substituents R' of the invention are those wherein G represents an unsubstituted or substituted alkylene chain —(CH$_2$)$_t$—, wherein t is 2 or 3, and R$^5$ represents a group

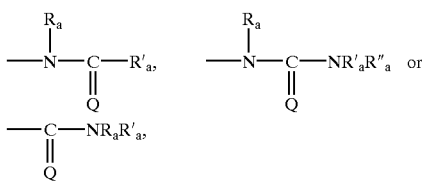

wherein R$_a$, R'$_a$, R"$_a$ and Q are as defined hereinbefore.

Even more advantageously, preferred substituents R' of the invention are those wherein G represents a group —(CH$_2$)$_t$—, wherein t is 2 or 3, and R$^5$ represents a group

wherein R'$_a$ represents an alkyl, polyhaloalkyl, alkenyl, alkynyl, cycloalkyl, cycloalkenyl, cycloakylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl, or G represents a group —(CH$_2$)$_3$— and R$^5$ represents a group

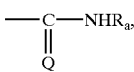

wherein R$_a$ represents an alkyl, polyhaloalkyl, alkenyl, alkynyl, cycloalkyl, cycloalkenyl, cycloakylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl.

More especially, preferred compounds of the invention are those wherein A represents a ring system of formula (II') or (III') and R represents a group of formula (V), (VI) or (VII).

More advantageously, the invention relates to compounds wherein:
  A represents a group of formula (II') or (III') substituted in the 5-position (formula II') or 7-position (formula III') by R and in the 3-position (formula II') or 1- or 2-position (formula III') by R',
  and R represents a group CONR'$_a$R"$_a$, SO$_2$NR'$_a$R"$_a$, COOR$^1_a$, NHCOR'$_a$ or NHCOOR'$_a$ (wherein R'$_a$, R"$_a$ and R$^1_a$ are as defined hereinbefore).

Even more advantageously, preferred compounds of the invention are those wherein A represents a ring system of formula (II') or (III') optionally substituted (in addition to R and R') by a substituent in the 2-position (formula II') or 3-position (formula III'), substituted in the 5-position (formula II') or 7-position (formula III') by R and in the 3-position (formula II')or 1- or 2-position (formula III') by R', R represents a group CONR'$_a$R"$_a$, SO$_2$NR'$_a$R"$_a$, COOR$^1_a$, NHCOR'$_a$ or NHCOOR'$_a$ (wherein R'$_a$, R"$_a$ and R$^1_a$ are as defined hereinbefore), and R' is such that G represents an unsubstituted or substituted alkylene chain —(CH$_2$)$_t$—, wherein t is 2 or 3, and R$^5$ represents a group

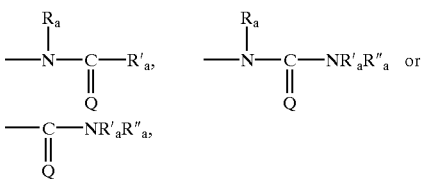

wherein R$_a$, R'$_a$, R"$_a$ and Q are as defined hereinbefore.

Even more especially, the invention relates to (dihydro) benzothiophenes, (dihydro)benzofurans, indoles, indolines, indenes, indans, azaindoles, thieno- or furopyridines optionally substituted in the 2-position, and to dihydronaphthalenes, tetrahydronaphthalenes, naphthalenes or chromans optionally substituted in the 3-position, substituted in the 5-position (or 7-position, respectively) by a group CONR'$_a$R"$_a$, SO$_2$NR'$_a$R"$_a$, COOR$^1_a$, NHCOR'$_a$ or NHCOOR'$_a$ wherein R'$_a$ and R"$_a$, which may be the same or different, represent a hydrogen atom, an alkyl, polyhaloalkyl, alkenyl, alkynyl, cycloalkyl, cycloalkenyl, cycloakylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl, or $R'_a$ and $R''_a$ form, together with the nitrogen atom carrying them, a piperazine, piperidine, morpholine or thiomorpholine group, and $R^1_a$ represents an alkyl, polyhaloalkyl, alkenyl, alkynyl, cycloalkyl, cycloalkenyl, cycloakylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl, and substituted in the 3-position (or 1- or 2-position, respectively) by a group —$(CH_2)_t$—$NHCOR'_a$ wherein t is 2 or 3 and $R'_a$ represents an alkyl, polyhaloalkyl, alkenyl, alkynyl, cycloalkyl, cycloalkenyl, cycloakylalkyl, cycloalkenylalkyl, aryl, arylalkyl, heteroaryl or heteroarylalkyl group, such as, for example, methyl, ethyl, propyl, isopropyl, butyl, isobutyl, sec-butyl, tert-butyl, pentyl, isopentyl, hexyl, trifluoromethyl, vinyl, allyl, propargyl, phenyl, naphthyl, benzyl, phenethyl, cyclopropyl, cyclobutyl, cyclopentyl, cyclohexyl, cyclohexenyl, methylcyclopropyl, ethylcyclopropyl, furyl, thienyl, pyridyl, furylmethyl, pyridylmethyl.

Even more advantageously, preferred compounds of the invention are: naphthalenes, dihydronaphthalenes or tetrahydronaphthalenes optionally substituted in the 3-postion, substituted in the 7-position by a group $NHCOR_a$, $NHCOOR_a$, $CONHR_a$ or $COOR^1_a$ (wherein $R_a$ and $R^1_a$ are as defined hereinbefore) and substituted in the 1-position by a group —$(CH_2)_t$—$NHCOR'_a$ wherein t is 2 or 3 and $R'_a$ is as defined hereinbefore, or benzofurans or benzothiophenes optionally substituted in the 2-position, substituted in the 5-position by a group $NHCOR_a$, $NHCOOR_a$, $CONHR_a$ or $COOR^1_a$ (wherein $R_a$ and $R^1_a$ are as defined hereinbefore) and substituted in the 3-position by a group —$(CH_2)_t$—$NHCOR'_a$ wherein t is 2 or 3 and $R'_a$ is as defined hereinbefore.

The invention relates very particularly to the compounds of formula (I) that are:

N-{2-[6-(acetylamino)-2,3-dihydro-1H-1-indenyl] ethyl}acetamide,
methyl 3-[2-(2-furoylamino)ethyl]-1-benzofuran-5-carboxylate,
methyl 3-{2-[(cyclopentylcarbonyl)amino]ethyl}-1-benzofuran-5-carboxylate,
methyl 3-{2-[(cyclopropylcarbonyl)amino]ethyl}-1-benzofuran-5-carboxylate,
methyl 3-[2-(3-butenoylamino)ethyl]-1-benzofuran-5-carboxylate,
N,N-diphenyl-3-[3-(acetylamino)propyl]benzo[b]furan-5-carboxamide,
3-[2-(acetylamino)ethyl]-1-benzofuran-5-carboxamide,
3-{2-[(cyclopropylcarbonyl)amino]ethyl}-1-benzofuran-5-carboxamide,
3-[2-(2-furoylamino)ethyl]-1-benzofuran-5-carboxamide,
3-{2-[(cyclopropylcarbonyl)amino]ethyl}-N-methyl-1-benzofuran-5-carboxamide,
3-[2-(acetylamino)ethyl]-N-methyl-1-benzofuran-5-carboxamide,
3-{2-[(cyclopentylcarbonyl)amino]ethyl}-N-methyl-1-benzofuran-5-carboxamide,
3-[2-(benzoylamino)ethyl]-N-methyl-1-benzofuran-5-carboxamide,
3-{2-[(cyclopropylcarbonyl)amino]ethyl}-N-methyl-1-benzofuran-5-carboxamide,
3-[2-(benzoylamino)ethyl]-N-methyl-1-benzofuran-5-carboxamide,
3-[2-(acetylamino)ethyl]-N-methyl-1H-pyrrolo[2,3-b]pyridine-5-carboxamide,
N-isopropyl-N-(2-propynyl)-3-[(acetylamino)methyl]-2-benzylbenzo[b]thiophene-5-carboxamide,
N-{3-[2-(acetylamino)ethyl]-1-benzofuran-5-yl}-2,2,2-trifluoroacetamide,
N-{2-[5-(acetylamino)-1-benzofuran-3-yl]ethyl}cyclopropanecarboxamide,
N-{2-[5-(acetylamino)-1-benzothiophen-3-yl]ethyl}benzamide,
N-{8-[2-([2-phenylacetyl]amino)ethyl]-2-naphthyl}-butanamide,
N-(8-{2-[(2-bromoacetyl)amino]ethyl}-2-naphthyl)-1-cyclohexanecarboxamide,
N-{8-[2-(heptanoylamino)ethyl]-2,6-dinaphthyl}-2-butenamide,
N-{8-[2-(acetylamino)ethyl]-2-naphthyl}acetamide,
N-ethyl-8-{2-[(2-phenylacetyl)amino]ethyl}-2-naphthamide,
N,N-diethyl-8-{2-[2-[(cyclopropylmethyl)amino]-2-oxoethyl}-2-naphthamide,
N-phenyl-8-(2-{methyl[(propylamino)carbonyl]amino}ethyl)-2-naphthamide,
N-benzyl-1-{2-[(2,2,2-trifluoroacetyl)amino]ethyl}-2-naphthamide,
N-(2-{7-[(methylamino)carbonyl]-1-naphthyl}ethyl)-2-furamide,
N-{2-[7-(aminosulphonyl)-1-naphthyl]ethyl}acetamide,
N-(2-{7-[(methylamino)sulphonyl]-1-naphthyl}ethyl)acetamide,
N-(2-{7-[(methylamino)sulphonyl]-1-naphthyl}ethyl)-2-furamide,
N-(2-{(7-[(ethylamino)sulphonyl]-1-naphthyl}ethyl)benzamide,
N-(2-{7-[(methylamino)sulphonyl]-1-naphthyl}ethyl)cyclopropanecarboxamide,
N-(3-{5-[(methylamino)sulphonyl]-1-benzofuran-3-yl}propyl)acetamide,
N-(2-{5-[(propylamino)sulphonyl]-1-benzofuran-3-yl}ethyl)acetamide,
N-(2-{5-[(cyclopropylamino)sulphonyl]-1-benzofuran-3-yl}ethyl)benzamide,
N-(2-{5-[(methylamino)sulphonyl]-1-benzofuran-3-yl}ethyl)-2-furamide,
N-(2-{5-[(methylamino)sulphonyl]-1-benzofuran-3-yl}ethyl)cyclopropanecarboxamide,
N-(2-{(2-benzyl-5-[(methylamino)sulphonyl]-1-benzothiophen-3-yl}ethyl)acetamide,
N-(2-{5-[(isopropylamino)sulphonyl]-1-benzothiophen-3-yl}ethyl)cyclopropanecarboxamide,
N-(2-{5-[(methylamino)sulphonyl]-1H-pyrrolo[2,3-b]pyridin-3-yl}ethyl)acetamide,
N-(2-{5-[(methylamino)sulphonyl]-1H-pyrrolo[2,3-b]pyridin-3-yl}ethyl)cyclopropanecarboxamide,
N-(2-{5-[(methylamino)sulphonyl]-1H-pyrrolo[2,3-b]pyridin-3-yl}ethyl)benzamide,
N-(2-{5-[(methylamino)sulphonyl]-1H-pyrrolo[2,3-b]pyridin-3-yl}ethyl)-2-furamide,
methyl N-{3-[2-(acetylamino)ethyl]benzo[b]furan-5-yl}carbamate,
methyl 3-{2-[(cyclopropylcarbonyl)amino]ethyl}-1-benzofuran-5-yl-carbamate,
tert-butyl 3-[2-(acetylamino)ethyl]-1-benzofuran-5-yl-carbamate,
tert-butyl 3-[2-(acetylamino)ethyl]-1-benzofuran-5-yl-(methyl)carbamate, methyl 3-[2-(benzoylamino)ethyl]-1-benzofuran-5-yl-carbamate,
methyl 3-[2-(isobutyrylamino)ethyl]-1-benzofuran-5-yl-carbamate,
methyl 5-[(acetylamino)methyl]-2,3-dihydro-1,4-benzodioxin-6-yl-carbamate,
methyl 3-[(acetylamino)methyl]-3,4-dihydro-2H-chromen-6-yl-carbamate,
ethyl 3-[2-(acetylamino)ethyl]-2,3-dihydro-]-1H-inden-5-yl-carbamate,
methyl 3-[2-(acetylamino)ethyl]-1H-pyrrolo[2,3-b]pyridin-5-yl-carbamate,
methyl 3-[2-(2-furoylamino)ethyl]-1H-pyrrolo[2,3-b]pyridin-5-yl-carbamate,
methyl 3-[2-(benzoylamino)ethyl]-1H-pyrrolo[2,3-b]pyridin-5-yl-carbamate,
methyl 3-{2-[(cyclopropylcarbonyl)amino]ethyl}-1H-pyrrolo[2,3-b]pyridin-5-yl-carbamate,
ethyl N-(8-{2-[(2-bromoacetyl)amino]ethyl}-2-naphthyl)carbamate,
methyl N-{8-[2-(acetylamino)ethyl]-6-phenyl-2-naphthyl}carbamate,
hexyl N-{8-[2-(acetylamino)ethyl]-5,6,7,8-tetrahydro-2-naphthyl}carbamate,
methyl 8-[2-(acetylamino)ethyl]-2-naphthyl-carbamate,
methyl 3-[2-(2-furoylamino)ethyl]-1-benzofuran-5-yl-carbamate,
methyl 3-{2-[(cyclopentylcarbonyl)amino]ethyl}-1-benzofuran-5-yl-carbamate,
methyl 3-[2-(benzoylamino)ethyl]-1-benzofuran-5-carboxylate,
methyl 3-[2-(isobutylamino)ethyl]-1-benzofuran-5-carboxylate,
3-[2-(benzoylamino)ethyl]-1-benzofuran-5-carboxamide.

The enantiomers and diastereoisomers, as well as the addition salts with a pharmaceutically acceptable acid or base, of the preferred compounds of the invention form an integral part of the invention.

The invention relates also to a process for the preparation of compounds of formula (I), which process is characterised in that there is used as starting material the compound of formula (X):

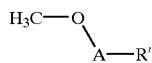 (X)

wherein A and R' are as defined hereinbefore, which is subjected to demethylation using conventional agents such as HBr, AlCl₃, AlBr₃, BBr₃ or Lewis acid/nucleophile binary systems such as AlCl₃/PhCH₂SH, or BBr₃/Me₂S, for example, to obtain the compound of formula (XI):

HO—A—R' (XI)

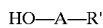

wherein A and R' are as defined hereinbefore,
which is converted, by means of the action of reagents such as POCl₃, PCl₅, Ph₃PBr₂, PhPCl₄, HBr or HI, into the corresponding halogenated compound of formula (XII):

Hal-A—R' (XII)

wherein A and R' are as defined hereinbefore and Hal represents a halogen atom (which compounds of formula (XII) can be obtained by exchange reactions such as, for example, the treatment of a chlorinated compound with KF in dimethylformamide to yield the corresponding fluorinated compound or the treatment of a brominated compound with KI in the presence of copper salts to yield the corresponding iodinated compound), which is treated:

with carbon monoxide and Bu₃SnH, the reaction being catalysed with palladium(0), to yield the corresponding aldehyde of formula (XIII):

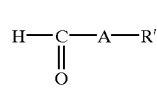 (XIII)

wherein A and R' are as defined hereinbefore, which compound of formula (XIII) may alternatively be obtained by customary lithiation methods starting from the halogenated compound of formula (XII), or via the corresponding vinyl compound (obtained starting from the compound of formula (XII) by the action of vinyltributyltin and tetrakis palladium) subjected to ozonolysis, or furthermore by direct formylation of the nucleus A, for example according to a Vilsmeier reaction, which compound of formula (XIII) is subjected to an oxidising agent to obtain the compound of formula (XIV):

HOOC—A—R' (XIV)

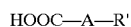

wherein A and R' are as defined hereinbefore, which is:

either subjected, in the presence of an acid catalyst, to the action of an alcohol of formula $R^1_a$OH, wherein $R^1_a$ is as defined hereinbefore, to yield the compound of formula (I/a), a particular case of the compounds of formula (I):

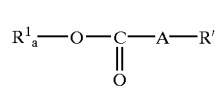 (I/a)

wherein A, $R^1_a$ and R' are as defined hereinbefore,
which may be subjected to a thionating agent, such as Lawesson's reagent, for example, to yield the compound of formula (I/b), a particular case of the compounds of formula (I):

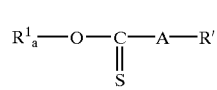 (I/b)

wherein A, $R^1_a$ and R' are as defined hereinbefore,
or converted, after the action of thionyl chloride and an azide, and then of an acid, into the compound of formula (XV):

H₂N—A—R' (XV)

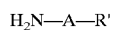

wherein A and R' are as defined hereinbefore, with which there is condensed:

either an acyl chloride ClCOR$_a$ or the corresponding anhydride (mixed or symmetrical), wherein R$_a$ is as defined hereinbefore, to yield the compound of formula (I/c), a particular case of the compounds of formula (I):

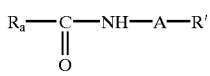
(I/c)

wherein $R_a$, A and R' are as defined hereinbefore,
which may be subjected to the action of a compound of formula (XVI):

 (XVI)

wherein $R'_a$ is as defined hereinbefore and J represents a leaving group such as a halogen atom or a tosyl group,
to obtain the compound of formula (I/d), a particular case of the compounds of formula (I):

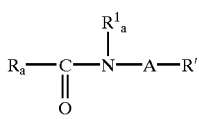
(I/d)

wherein $R_a$, $R^1_a$, A and R' are as defined hereinbefore,
which compounds of formulae (I/c) and (I/d) constitute the compound of formula (I/e), a particular case of the compounds of formula (I):

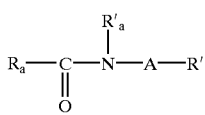
(I/e)

wherein $R_a$, $R'_a$, A and R' are as defined hereinbefore,
which compound of formula (I/e) may be subjected to a thionating agent, such as Lawesson's reagent, for example, to obtain the compound of formula (I/f), a particular case of the compounds of formula (I):

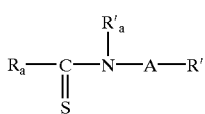
(I/f)

wherein $R_a$, $R'_a$, A and R' are as defined hereinbefore,
or a compound of formula (XVII):

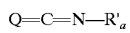 (XVII)

wherein Q and $R'_a$ are as defined hereinbefore,
to yield the compound of formula (I/g), a particular case of the compounds of formula (I):

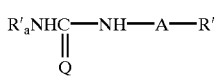
(I/g)

wherein $R'_a$, Q, A and R' are as defined hereinbefore,
which may be subjected to the action of a compound of formula (XVI) to obtain the compound of formula (I/h), a particular case of the compounds of formula (I):

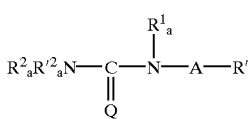
(I/h)

wherein Q, $R^1_a$, A and R' are as defined hereinbefore and $R^2_a$ and $R'^2_a$, which may be the same or different, may take any of the values of $R_a$ except for the hydrogen atom and cannot form a cyclic structure together with the nitrogen atom carrying them,
or a compound of formula (XVIII):

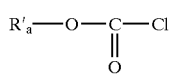 (XVIII)

wherein $R'_a$ is as defined hereinbefore, or its corresponding anhydride $(R'_aOCO)_2O$,
to obtain the compound of formula (I/i), a particular case of the compounds of formula (I):

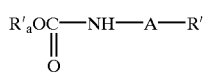 (I/i)

wherein $R'_a$, A et R' are as defined hereinbefore,
which may be subjected to the action of a compound of formula (XVI) and/or the action of a thionating agent to yield the compound of formula (I/j), a particular case of the compounds of formula (I):

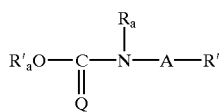
(I/j)

wherein $R_a$, $R'_a$, Q, A and R' are as defined hereinbefore,
or a compound of formula (XIX):

 (XIX)

wherein $R_a$ is as defined hereinbefore,
optionally followed by the action of a compound of formula (XVI) to yield the compound of formula (I/k), a particular case of the compounds of formula (I):

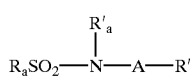
(I/k)

wherein $R_a$, A and R' are as defined hereinbefore,
or which compound of formula (XI) is converted, by means of the action of benzylthiol and trifluoromethanesulphonic acid, into the corresponding benzylthio compound of formula (XX):

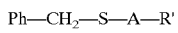 (XX)

wherein A and R' are as defined hereinbefore,
which is placed in the presence of iodosobenzene and hydrochloric acid to yield the compound of formula (XXI):

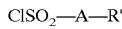 (XXI)

wherein A and R' are as defined hereinbefore,
with which there is condensed an amine R'$_a$R"$_a$NH (wherein R'$_a$ and R"$_a$ are as defined hereinbefore),
to obtain the compound of formula (I/l), a particular case of the compounds of formula (I):

   (I/l)

wherein R'$_a$, R"$_a$, A and R' are as defined hereinbefore,
it being possible for the compound of formula (I/la), a particular case of the compounds of formula (I/l):

   (I/la)

wherein A and R' are as defined hereinbefore, to be subjected to the action
of an acyl chloride ClCOR'$_a$, optionally followed by the action of a compound of formula (XVI) and/or Lawesson's reagent,
to yield the compound of formula (I/m), a particular case of the compounds of formula (I):

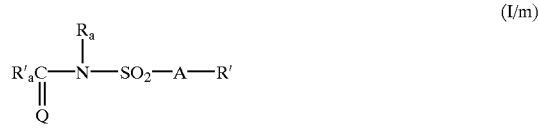   (I/m)

wherein R$_a$, R'$_a$, Q, A and R' are as defined hereinbefore,
of a compound of formula (XVII), optionally followed by the action of a compound of formula (XVI) to obtain the compound of formula (I/n), a particular case of the compounds of formula (I):

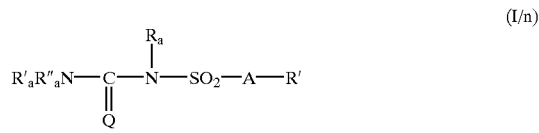   (I/n)

wherein R$_a$, R'$_a$, R"$_a$, Q, A and R' are as defined hereinbefore,
or of a compound of formula (XVIII), optionally followed by the action of a compound of formula (XVI),
to yield the compound of formula (I/o), a particular case of the compounds of formula (I):

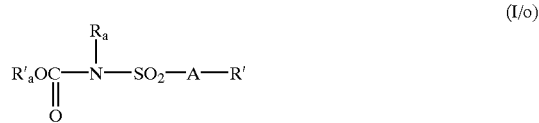   (I/o)

wherein R$_a$, R'$_a$, A and R' are as defined hereinbefore,
which compounds (I/a) to (I/o) can be purified in accordance with a conventional separation technique, are converted, if desired, into their addition salts with a pharmaceutically acceptable acid or base and, optionally, are separated into their isomers in accordance with a conventional separation technique.

The starting compounds (X) are either commercially available or are described in the literature, for example in the Patent Applications EP0447285, EP0527687, EP0562956, EP0591057, EP0662471, EP0745586, EP0709371, EP0745583, EP0721938, EP0745584, EP0737670, EP0737685, or WO9738682.

Another advantageous process of the invention relating to preparation of the compounds of formula (I) is characterised in that there is used as starting material the compound of formula (XXII):

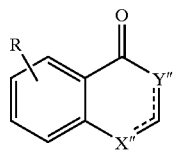   (XXII)

wherein R and the symbol ⋯ are as defined hereinbefore,
Y" represents a group C(H)$_q$ (wherein q is 0, 1 or 2) or a bond, and X" represents an oxygen, nitrogen or sulphur atom or a group C(H)$_q$ (wherein q is 0, 1 or 2) or NR$_0$ (wherein R$_0$ is as defined hereinbefore), it being understood that when X" represents a nitrogen atom or a group NR$_0$ then Y" represents a bond,
which is subjected to a Wittig reaction and then to reduction to yield the compound of formula (XXIII):

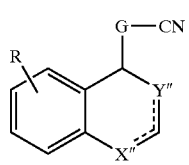   (XXIII)

wherein R, X", Y", G and the symbol ⋯ are as defined hereinbefore,
which may be oxidised to yield the compound of formula (XXIV):

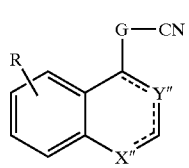   (XXIV)

wherein R$^1$, X", Y", G and the symbol ⋯ are as defined hereinbefore,
which is:
either hydrolysed in an acid or basic medium and then subjected, after activation to the acid chloride form or in the presence of a coupling agent, to the action of an amine HNR'$_a$R"$_a$ wherein R'$_a$ and R"$_a$ are as defined hereinbefore to yield the compound of formula (I/p), a particular case of the compounds of formula (I):

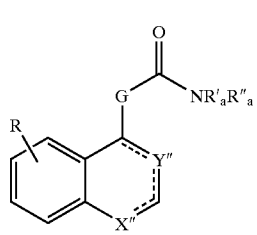   (I/p)

wherein R, X", Y", G, R'$_a$, R"$_a$ and the symbol ⋯ are as defined hereinbefore,
which may be subjected to a thionating agent such as Lawesson's reagent to yield the compound of formula (I/q), a particular case of the compounds of formula (1):

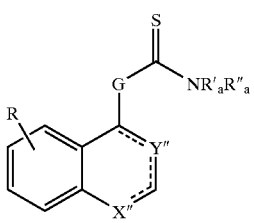

(I/q)

wherein R, X", Y", G, R'$_a$, R"$_a$ and the symbol ⋯ are as defined hereinbefore, or hydrolysed in an acid or basic medium and then converted into the corresponding azide to yield, after having been subjected to a Curtius rearrangement and hydrolysis, the compound of formula (XXV):

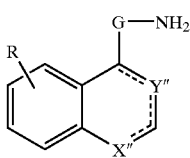

(XXV)

wherein R, X", Y" and G are as defined hereinbefore, which is reacted with:

an acyl chloride ClCOR'$_a$ or the corresponding anhydride (mixed or symmetrical) wherein R'$_a$ is as defined hereinbefore, optionally followed by the action of a compound of formula (XVI) and/or the action of a thionating agent to yield the compound of formula (I/r), a particular case of the compounds of formula (I):

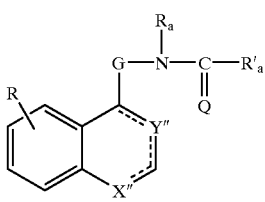

(I/r)

wherein R, X", Y", G, R$_a$, R'$_a$, Q and the symbol ⋯ are as defined hereinbefore, or with a compound of formula (XVII), optionally followed by the action of a compound of formula (XVI) to yield the compound of formula (I/s), a particular case of the compounds of formula (I):

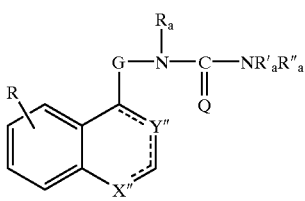

(I/s)

wherein R, X", Y", G, R$_a$, R'$_a$, R"$_a$, Q and the symbol ⋯ are as defined hereinbefore,
which compounds (I/p) to (I/s) can be purified in accordance with a conventional separation technique, are converted, if desired, into their addition salts with a pharmaceutically acceptable acid or base and, optionally, are separated into their isomers in accordance with a conventional separation technique.

The compounds of formula (XXII) are either commercially available or easily accessible to the person skilled in the art, starting from the compound of formula (XXVI):

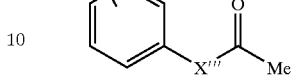

(XXVI)

wherein R is as defined hereinbefore and X''' represents an oxygen or sulphur atom or a group NR$_0$ (wherein R$_0$ is as defined hereinbefore), (the compound of formula (XXVI) either being commercially available or being obtained starting from the compound of formula (XXVI')):

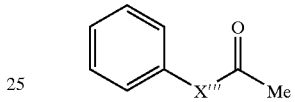

(XXVI')

wherein X''' is as defined hereinbefore, by conventional reactions for substitution of the aromatic nucleus), which is subjected to the action of AlCl$_3$ to yield the compound of formula (XXVII):

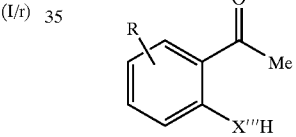

(XXVII)

wherein R and X''' are as defined hereinbefore, which is subjected to bromination to obtain the compound of formula (XXVIII):

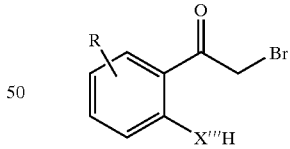

(XXVIII)

wherein X''' and R are as defined hereinbefore, which is placed in a basic medium to yield the compound of formula (XXIX), a particular case of the compounds of formula (XXII):

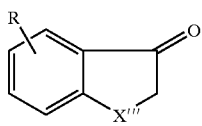

(XXIX)

wherein R and X''' are as defined hereinbefore, or starting from the compound of formula (XXX):

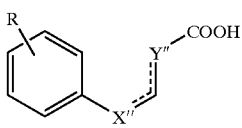

(XXX)

wherein R, X", Y" and the symbol ⋯ are as defined hereinbefore,
which is cyclised in the presence of polyphosphoric acid to yield the compound of formula (XXII).

The invention relates also to a process for the preparation of compounds of formula (I) wherein R represents a ring of formula (VIII), which process is characterised in that compounds of formulae (I/a) to (I/s) are used as starting materials, which are cyclised according to methods described in the literature, for example in the Patent Applications EP0708099 or WO9732871.

The compounds of the invention and pharmaceutical compositions comprising them are proving to be useful in the treatment of disorders of the melatoninergic system.

Pharmacological study of the compounds of the invention has in fact shown them to be non-toxic, to have strong affinity for melatonin receptors and to possess important activities in respect of the central nervous system and, in particular, there have been found therapeutic properties in relation to sleep disorders, anxiolytic, antipsychotic and analgesic properties and in relation to the microcirculation, enabling it to be established that the products of the invention are useful in the treatment of stress, sleep disorders, anxiety, seasonal affective disorder, cardiovascular pathologies, pathologies of the digestive system, insomnia and fatigue resulting from jet lag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and also cerebral circulation disorders. In another field of activity, it appears that, in treatment, the products of the invention can be used in sexual dysfunction, that they have ovulation-inhibiting properties and immunomodulating properties and are able to be used in the treatment of cancers.

The compounds will preferably be used in the treatment of seasonal affective disorder, sleep disorders, cardiovascular pathologies, insomnia and fatigue resulting from jet lag, appetite disorders and obesity.

For example, the compounds will be used in the treatment of seasonal affective disorder and sleep disorders.

The present invention relates also to pharmaceutical compositions comprising at least one compound of formula (I), alone or in combination with one or more pharmaceutically acceptable excipients.

Among the pharmaceutical compositions according to the invention there may be mentioned more especially those that are suitable for oral, parenteral, nasal, per- or transcutaneous, rectal, perlingual, ocular or respiratory administration and especially tablets, dragees, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication, or possible associated treatments, and ranges from 0.01 mg to 1 g per 24 hours in 1 or more administrations.

The following Examples illustrate the invention but do not limit it in any way. The following Preparations yield compounds of the invention or synthesis intermediates that are useful in preparation of the compounds of the invention.

Preparation 1: N-[2-(7-Hydroxy-1-naphthyl)ethyl] acetamide

Under an inert atmosphere, 27.5 mmol of boron tribromide/dimethyl sulphide complex are dissolved in 100 ml of dichloromethane and stirred for 15 min at ambient temperature. A solution of 13.7 mmol of N-[2-(7-methoxy-1-naphthyl)ethyl]acetamide in 50 ml of dichloromethane is added and the reaction mixture is heated at reflux for 30 hours. After cooling, the reaction mixture is hydrolysed with caution and the dichloromethane is evaporated off. The mixture is then extracted with ethyl acetate, the combined organic phases are washed with a 1M aqueous solution of potassium bicarbonate and then with 1M sodium hydroxide solution. The organic phase is dried over magnesium sulphate and concentrated to yield the title compound.

Preparation 2: N-[2-(7-Hydroxy-1-naphthyl)ethyl]-2-phenylacetamide

The procedure is as in Preparation 1, but the N-[2-(7-methoxy-1-naphthyl)ethyl]acetamide is replaced by N-[2-(7-methoxy-1-naphthyl)ethyl]-2-phenylacetamide.

In Preparations 3 to 37, the procedure is as in Preparation 1, but the N-[2-(7-methoxy-1-naphthyl)ethyl]acetamide is replaced by the appropriate methoxylated starting substrate.

Preparation 3: N-[2-(7-Hydroxy-1-naphthyl)ethyl]-2-bromoacetamide

Preparation 4: N-[2-(8-Hexyl-7-hydroxy-1-naphthyl)ethyl]-2-phenylacetamide

Preparation 5: N-Cyclopropylmethyl-2-(7-hydroxy-1-naphthyl)acetamide

Preparation 6: N-Cyclohexyl-4-(7-hydroxy-1-naphthyl)butanamide

Preparation 7: N-[2-(7-Hydroxy-1-naphthyl)ethyl]-N-methyl-N'-propylurea

Preparation 8: N-[3-(7-Hydroxy-1-naphthyl)propyl] acetamide

Preparation 9: N-[2-(7-Hydroxy-1-naphthyl)ethyl]-3-butenamide

Preparation 10: N-[3-(7-Hydroxy-1-naphthyl) propyl]-1-cyclohexanecarboxamide

Preparation 11: N-[2-(2-Hydroxy-1-naphthyl)ethyl]-2,2,2-trifluoroacetamide

Preparation 12: N-[2-(2-Hydroxy-1-naphthyl)-1-methylethyl]propanamide

Preparation 13: N-[2-(7-Hydroxy-3-phenyl-1-naphthyl)ethyl]acetamide

Preparation 14: N-[2-(3-Benzoyl-7-hydroxy-1-naphthyl)ethyl]-N'-propylurea

Preparation 15: N-{2-[3-(Cyclopropylmethyl)-7-hydroxy-1-naphthyl]ethyl}acetamide Preparation 16: N-[3-(5-Hydroxybenzo[b]furan-3-yl)propyl]acetamide Preparation 17: N-Methyl-4-(5-hydroxybenzo[b]furan-3-yl)butanamide Preparation 18: N-[2-(5-Hydroxybenzo[b]furan-3-yl)ethyl]acetamide Preparation 19: N-[(2-Benzyl-5-hydroxybenzo[b]thiophen-3-yl)methyl]acetamide Preparation 20: N-[2-(5-Hydroxythieno[3,2-b]pyridin-3-yl)ethyl]acetamide Preparation 21: N-[2-(5-Hydroxy-1H-3-indolyl)ethyl]benzamide Preparation 22: N-{2-[2-(4-Fluorobenzyl)-5-hydroxy-1-methyl-1H-pyrrolo[2,3-b]pyridin-3-yl]ethyl}acetamide Preparation 23: N-[2-(2-Benzyl-5-hydroxybenzo[b]furan-3-yl)ethyl]-1-cyclopropanecarboxamide Preparation 24: N-[(6-Hydroxy-3,4-dihydro-2H-3-chromenyl)methyl]acetamide Preparation 25: N-[2-(6-Hydroxy-3,4-dihydro-2H-4-chromenyl)ethyl]-2-phenylacetamide Preparation 26: N-[(6-Hydroxy-2-phenyl-2H-3-chromenyl)methyl]acetamide Preparation 27: N-[(6-Hydroxy-2-phenyl-2H-3-chromenyl)methyl]butanamide Preparation 28: N-[2-(6-Hydroxy-3,4-dihydro-2H-4-thiochromenyl)ethyl]acetamide Preparation 29: N-[2-(7-Hydroxy-1,4-benzodioxin-2-yl)ethyl-N'-propylurea Preparation 30: N-[2-(7-Hydroxy-2,3-dihydro-1,4-benzodioxin-2-yl)ethyl]acetamide Preparation 31: N-[2-(6-Hydroxy-2,3-dihydro-1,4-benzodioxin-5-yl)ethyl]acetamide Preparation 32: N-[(9-Hydroxy-2,3-dihydro-1H-benzo[f]chromen-2-yl)methyl]-2-cyclopropylacetamide Preparation 33: N-Cyclopropyl-N'-(4-hydroxy-2,3-dihydro-1H-2-phenalenyl)thiourea Preparation 34: N-Cyclobutyl-3-hydroxy-4,5-dihydro-3H-benzo[cd]isobenzofuran-4-carboxamide Preparation 35: N-{2-[7-Hydroxy-3-naphthyl-1-naphthyl]ethyl}heptanamide Preparation 36: N-[2-(7-Hydroxy-1,2,3,4-tetrahydro-1-naphthyl)ethyl]acetamide Preparation 37: N-[2-(6-Hydroxy-2,3-dihydro-1H-1-indenyl)ethyl]acetamide Preparation 38: N-Cyclohexyl-4-(7-chloro-1-naphthyl)butanamide Chlorine (10 mmol) is bubbled into dichlorophenylphosphine at a flow rate such that the reaction temperature is maintained between 70 and 80° C. After all the chlorine has been added, the phenylphosphine tetrachloride so obtained is a pale yellow liquid. 10 mmol of the product obtained in Preparation 5 are added all at once and the reaction mixture is heated at 160° C. overnight. After cooling, the solution is poured into a water/ice mixture (20 ml) and is neutralised with a 50% aqueous solution of sodium hydroxide. After extraction with ether, the organic phases are dried and concentrated under reduced pressure to yield a residue, which is chromatographed on silica gel to obtain the pure title product.

In Preparation 39, the procedure is as in Preparation 38, but the appropriate starting compound is used.

Preparation 39: N-[(6-Chloro-3,4-dihydro-2H-3-chromenyl)methyl]acetamide

Starting compound: Preparation 24

Preparation 40: N-[2-(7-Bromo-1-naphthyl)ethyl]-2-phenylacetamide

Triphenylphosphine (10 mmol) and acetonitrile (70 ml) are poured into a 150 ml three-necked flask equipped with a bromine funnel, a condenser surmounted by a tube filled with calcium chloride and a mechanical stirrer. The solution is cooled with the aid of an ice bath, with stirring, and bromine is added (10 mmol). At the end of the addition, the ice bath is removed and the product obtained in Preparation 2 (8 mmol) is then added. The reaction mixture is stirred at 60–70° C. until the starting compound has disappeared (monitored by TLC). At the end of the reaction, the mixture is filtered and the filtrate is then concentrated under reduced pressure. The residue is taken up in ethyl acetate, washed with water and then with saturated potassium hydrogen carbonate solution and once again with water, and is then dried over magnesium sulphate and concentrated under reduced pressure. The residue is filtered through silica gel to yield the title product.

In Preparations 41 to 72.1, the procedure is as in Preparation 40, starting from the appropriate reactant.

Preparation 41: N-Cyclopropylmethyl-2-(7-bromo-1-naphthyl)acetamide

Starting compound: Preparation 5

Preparation 42: N-[2-(7-Bromo-1-naphthyl)ethyl]-N-methyl-N'-propylurea

Starting compound: Preparation 7

Preparation 43: N-[3-(7-Bromo-1-naphthyl)propyl]-1-cyclohexanecarboxamide

Starting compound: Preparation 10

Preparation 44: N-[2-(2-Bromo-1-naphthyl)ethyl]-2,2,2-trifluoroacetamide

Starting compound: Preparation 11

Preparation 45: N-[2-(3-Benzoyl-7-bromo-1-naphthyl)ethyl]-N'-propylurea

Starting compound: Preparation 14

Preparation 46: N-[3-(5-Bromobenzo[b]furan-3-yl)propyl]acetamide

Starting compound: Preparation 16

Preparation 47: N-[(2-Benzyl-5-bromobenzo[b]thiophen-3-yl)methyl]acetamide

Starting compound: Preparation 19

Preparation 48: N-[2-(5-Bromo-2-(4-fluorobenzyl)-1-methyl-1H-pyrrolo[2,3-b]pyridin-3-yl)ethyl]acetamide Starting compound: Preparation 22

Preparation 49: N-[2-(6-Bromo-3,4-dihydro-2H-4-chromenyl)ethyl]-2-phenylacetamide Starting compound: Preparation 25

Preparation 50: N-[(6-Bromo-2-phenyl-2H-3-chromenyl)methyl]acetamide

Starting compound: Preparation 26

Preparation 51: N-[2-(6-Bromo-3,4-dihydro-2H-4-thiochromenyl)ethyl]acetamide

Starting compound: Preparation 28

Preparation 52: N-[2-(7-Bromo-1,4-benzodioxin-2-yl)ethyl]-N'-propylurea

Starting compound: Preparation 29

Preparation 53: N-[2-(6-Bromo-2,3-dihydro-1,4-benzodioxin-5-yl)ethyl]acetamide

Starting compound: Preparation 31

Preparation 54: N-[(9-Bromo-2,3-dihydro-1H-benzo[f]chromen-2-yl)methyl]-2-cyclopropylacetamide Starting compound: Preparation 32

Preparation 55: N-(4-Bromo-2,3-dihydro-1H-2-phenalenyl)-N'-cyclopropylthiourea

Starting compound: Preparation 33

Preparation 56: N-Cyclobutyl-6-bromo-4,5-dihydro-3H-benzo[cd]isobenzofuran-4-carboxamide Starting compound: Preparation 34

Preparation 57: N-[2-(7-Bromo-3-naphthyl-1-naphthyl)ethyl]heptanamide

Starting compound: Preparation 35

Preparation 58: N-[2-(7-Bromo-1-naphthyl)ethyl]acetamide

Starting compound: Preparation 1

Preparation 59: N-[2-(7-Bromo-1-naphthyl)ethyl]-3-butenamide

Starting compound: Preparation 9

Preparation 60: N-[2-(7-Bromo-1-naphthyl)ethyl]-2-bromoacetamide

Starting compound: Preparation 3

Preparation 61: N-[2-(7-Bromo-8-hexyl-1-naphthyl)ethyl]-2-phenylacetamide

Starting compound: Preparation 4

Preparation 62: N-[3-(7-Bromo-1-naphthyl)propyl]acetamide

Starting compound: Preparation 8

Preparation 63: N-[2-(2-Bromo-1-naphthyl)-1-methylethyl]propanamide

Starting compound: Preparation 12

Preparation 64: N-{2-[7-Bromo-3-(cyclopropylmethyl)-1-naphthyl]ethyl}acetamide

Starting compound: Preparation 15

Preparation 65: N-Methyl-3-(5-bromobenzo[b]furan-3-yl)butanamide

Starting compound: Preparation 17

Preparation 66: N-[2-(5-Bromothieno[3,2-b]pyridin-3-yl)ethyl]acetamide

Starting compound: Preparation 20

Preparation 67: N-[2-(5-Bromo-1H-3-indolyl)ethyl]benzamide

Starting compound: Preparation 21

Preparation 68: N-[2-(2-Benzyl-5-bromobenzo[b]furan-3-yl)ethyl]-1-cyclopropanecarboxamide Starting compound: Preparation 23

Preparation 69: N-[(6-Bromo-2-phenyl-2H-3-chromenyl)methyl]butanamide

Starting compound: Preparation 27

Preparation 70: N-[2-(6-Bromo-2,3-dihydro-1H-1-indenyl)ethyl]acetamide

Starting compound: Preparation 37

Preparation 71: N-[2-(7-Bromo-3-phenyl-1-naphthyl)ethyl]acetamide

Starting compound: Preparation 13

Preparation 72: N-[2-(5-Bromobenzo[b]furan-3-yl)ethyl]acetamide

Starting compound: Preparation 18

Preparation 72.1: N-[2-7-Bromo-1,2,3,4-tetrahydro-1-naphthyl)ethyl]acetamide

Starting compound: Preparation 36

Preparation 73: N-[2-(7-Iodo-1-naphthyl)ethyl]-2-phenylacetamide

A mixture of the product obtained in Preparation 40 (2 mmol), potassium iodide (30 mmol) and copper(I) iodide (10 mmol) in hexamethylphosphoramide (6 ml) is heated at 150–160° C., with stirring, under a nitrogen atmosphere until 90% conversion has been achieved (monitored by TLC). Then, dilute hydrochloric acid, and then ether, are added and the mixture is then filtered to remove the insoluble copper(I) salts. The organic phase is separated off, washed with sodium sulphite solution and with water, dried over magnesium sulphate and evaporated to yield a residue which is chromatographed on silica gel to yield the title product.

In Preparations 74 to 108 the procedure is as in Preparation 73, but the product of Preparation 40 is replaced by the appropriate substrate.

Preparation 74: N-Cyclopropylmethyl-2-(7-iodo-1-naphthyl)acetamide

Starting compound: Preparation 41

Preparation 75: N-[2-(7-Iodo-1-naphthyl)ethyl]-N-methyl-N'-propylurea

Starting compound: Preparation 42

Preparation 76: N-[3-(7-Iodo-1-naphthyl)propyl]-1-cyclohexanecarboxamide

Starting compound: Preparation 43

Preparation 77: N-[2-(2-Iodo-1-naphthyl)ethyl]-2,2,2-trifluoroacetamide

Starting compound: Preparation 44

Preparation 78: N-[2-(3-Benzoyl-7-iodo-1-naphthyl)ethyl]-N'-propylurea

Starting compound: Preparation 45

Preparation 79: N-[3-(5-Iodobenzo[b]furan-3-yl)propyl]acetamide

Starting compound: Preparation 46

Preparation 80: N-[(2-Benzyl-5-iodobenzo[b]thiophen-3-yl)methyl]acetamide

Starting compound: Preparation 47

Preparation 81: N-[2-(5-Iodo-2-(4-fluorobenzyl)-1-methyl-1H-pyrrolo[2,3-b]pyridin-3-yl)ethyl]acetamide Starting compound: Preparation 48

Preparation 82: N-[(6-Iodo-3,4-dihydro-2H-3-chromenyl)methyl]acetamide

Starting compound: Preparation 39

Preparation 83: N-[2-(6-Iodo-3,4-dihydro-2H-4-chromenyl)ethyl]-2-phenylacetamide Starting compound: Preparation 49

Preparation 84: N-[(6-Iodo-2-phenyl-2H-3-chromenyl)methyl]acetamide

Starting compound: Preparation 50

Preparation 85: N-[2-(6-Iodo-3,4-dihydro-2H-4-thiochromenyl)ethyl]acetamide

Starting compound: Preparation 51

Preparation 86: N-[2-(7-Iodo-1,4-benzodioxin-2-yl)ethyl]-N'-propylurea

Starting compound: Preparation 52

Preparation 87: N-[2-(6-Iodo-2,3-dihydro-1,4-benzodioxin-5-yl)ethyl]acetamide

Starting compound: Preparation 53

Preparation 88: N-[(9-Iodo-2,3-dihydro-1H-benzo[f]chromen-2-yl)methyl]-2-cyclopropylacetamide Starting compound: Preparation 54

Preparation 89: N-(4-Iodo-2,3-dihydro-1H-2-phenalenyl)-N'-cyclopropylthiourea

Starting compound: Preparation 55

Preparation 90: N-Cyclobutyl-6-iodo-4,5-dihydro-3H-benzo[cd]isobenzofuran-4-carboxamide Starting compound: Preparation 56

29

Preparation 91: N-[2-(7-Iodo-3-naphthyl-1-naphthyl)ethyl]heptanamide

Starting compound: Preparation 57

Preparation 92: N-[2-(7-Iodo-1-naphthyl)ethyl]acetamide

Starting compound: Preparation 58

Preparation 93: N-[2-(7-Iodo-1-naphthyl)ethyl]-3-butenamide

Starting compound: Preparation 59

Preparation 94: N-[2-(7-Iodo-1-naphthyl)ethyl]-2-bromoacetamide

Starting compound: Preparation 60

Preparation 95: N-[2-(7-Iodo-8-hexyl-1-naphthyl)ethyl]-2-phenylacetamide

Starting compound: Preparation 61

Preparation 96: N-Cyclohexyl-4-(7-iodo-1-naphthyl)butanamide

Starting compound: Preparation 38

Preparation 97: N-[3-(7-Iodo-1-naphthyl)propyl]acetamide

Starting compound: Preparation 62

Preparation 98: N-[2-(2-Iodo-1-naphthyl)-1-methylethyl]propanamide

Starting compound: Preparation 63

Preparation 99: N-{2-[7-Iodo-3-(cyclopropylmethyl)-1-naphthyl]ethyl}acetamide

Starting compound: Preparation 64

Preparation 100: N-Methyl-4-(5-iodobenzo[b]furan-3-yl)butanamide

Starting compound: Preparation 65

Preparation 101: N-[2-(5-Iodothieno[3,2-b]pyridin-3-yl)ethyl]acetamide

Starting compound: Preparation 66

Preparation 102: N-[2-(5-Iodo-1H-3-indolyl)ethyl]benzamide

Starting compound: Preparation 67

Preparation 103: N-[2-(2-Benzyl-5-iodobenzo[b]furan-3-yl)ethyl]-1-cyclopropane-carboxamide Starting compound: Preparation 68

Preparation 104: N-[(6-Iodo-2-phenyl-2H-3-chromenyl)methyl]butanamide

Starting compound: Preparation 69

Preparation 105: N-[2-(6-Iodo-2,3-dihydro-1H-1-indenyl)ethyl]acetamide

Starting compound: Preparation 70

Preparation 106: N-[2-(7-Iodo-3-phenyl-1-naphthyl)ethyl]acetamide

Starting compound: Preparation 71

30

Preparation 107: N-[2-(7-Iodo-1,2,3,4-tetrahydro-1-naphthyl)ethyl]acetamide

Starting compound: Preparation 72.1

Preparation 108: N-[2-(5-Iodobenzo[b]furan-3-yl)ethyl]acetamide

Starting compound: Preparation 72

Preparation 109: N-[2-(7-Amino-1-naphthyl)ethyl]-2-phenylacetamide

Step A: N-[2-(7-Vinyl-1-naphthyl)ethyl]-2-phenylacetamide 15 mmol of the product obtained in Preparation 73, 16 mmol of vinyltributyltin and 0.43 mmol of tetrakis(triphenylphosphine)palladium are heated in 30 ml of N-methylpyrrolidinone at 110° C. for 3 hours, with stirring. After evaporating off the solvent, the residue is taken up in 20 ml of dichloromethane and treated with 10% aqueous potassium fluoride solution. After extraction, concentration under reduced pressure and chromatography on silica gel, the pure title product is obtained.

Step B: N-[2-(7-Formyl-1-naphthyl)ethyl]-2-phenyl-acetamide

To a solution of 10 mmol of the product obtained in Step A in a mixture of 50 ml of dioxane and 25 ml of water there are added, at ambient temperature, 1.10 g of osmium tetroxide in 2-methyl-2-propanol and then 8.70 g of sodium periodate. After stirring overnight at ambient temperature, the suspension is filtered and the filtrate is concentrated under reduced pressure. The residue obtained is taken up in dichloromethane. The organic phase is washed with water, dried and evaporated. The residue is purified by chromatography on silica gel to yield the title product.

Step C: 8-{2-[(2-Phenylacetyl)amino]ethyl}-2-naphthoic acid 2.7 g of potassium permanganate in 50 ml of an acetone/water mixture (50/50) are added, at ambient temperature, to a solution of 6.88 mmol of the product obtained in Step B in 30 ml of acetone. The solution is stirred for 2 hours at ambient temperature and is then filtered. The filtrate is concentrated under reduced pressure and chromatographed on silica gel to yield the title product.

Step D: 8{-(2-[(2-Phenylacetyl)amino]ethyl}-2-naphthalenecarbonyl chloride 5 mmol of the product obtained in Step C are dissolved in 40 ml of thionyl chloride. After stirring under an inert atmosphere for 1 hour, the thionyl chloride is evaporated off under reduced pressure to yield the title product.

Step E: N-[2-(7-Amino-1-naphthyl)ethyl]-2-phenyl-acetamide

A solution of the product obtained in Step D (20 mmol) in dichloromethane (30 ml) containing tetrabutylammonium bromide (20 mg) is cooled in an ice bath. After adding sodium azide (24 mmol) dissolved in 5 ml of water, the solution is stirred vigorously at 0° C. for 2 hours. The organic phase is separated off, washed with water (2×5 ml) and dried over magnesium sulphate. After filtration, trifluoroacetic acid (30 mmol) is added and the solution is stirred under reflux for 60 hours. After cooling, the organic phase is washed with saturated sodium hydrogen carbonate solution (2×5 ml) and is concentrated under reduced pressure. The residue is then taken up in methanol (20 ml); water (80 ml) and then potassium carbonate (30 mmol) are added. After stirring at ambient temperature for 20 hours, the reaction mixture is concentrated under reduced pressure to a volume of about 60 ml and is then extracted 3 times with ether (3×50 ml). After drying over sodium sulphate, the organic phase is filtered and then evaporated under reduced pressure. The residue is chromatographed on silica gel to yield the title product.

In Preparations 110 to 134 the procedure is as in Example 109, starting from the appropriate substrate.

Preparation 110: N-[2-(7-Amino-1-naphthyl)ethyl]-2-bromoacetamide

Starting compound: Preparation 94

Preparation 111: N-[2-(7-Amino-8-hexyl-1-naphthyl)ethyl]-2-phenylacetamide

Starting compound: Preparation 95

Preparation 112: N-Cyclohexyl-4-(7-amino-1-naphthyl)butanamide

Starting compound: Preparation 96

Preparation 113: N-[3-(7-Amino-1-naphthyl)propyl]acetamide

Starting compound: Preparation 97

Preparation 114: N-[2-(2-Amino-1-naphthyl)-1-methylethyl]propanamide

Starting compound: Preparation 98

Preparation 115: N-[2-(7-Amino-3-benzoyl-1-naphthyl)ethyl]-N'-propylurea

Starting compound: Preparation 78

Preparation 116: N-[2-(7-Amino-1-naphthyl)ethyl]-3-butenamide

Starting compound: Preparation 93

Preparation 117: N-[2-(7-Amino-1-naphthyl)ethyl]acetamide

Starting compound: Preparation 92

Preparation 118: N-{2-[7-Amino-3-(cyclopropylmethyl)-1-naphthyl]ethyl}acetamide

Starting compound: Preparation 99

Preparation 119: N-Methyl-4-(5-aminobenzo[b]furan-3-yl)butanamide

Starting compound: Preparation 100

Preparation 120: N-[2-(5-Aminothieno[3,2-b]pyridin-3-yl)ethyl]acetamide

Starting compound: Preparation 101

Preparation 121: N-[2-(5-Amino-1H-3-indolyl)ethyl]benzamide

Starting compound: Preparation 102

Preparation 122: N-{2-[5-Amino-2-(4-fluorobenzyl)-1-methyl-1H-pyrrolo[2,3-b]pyridin-3-yl]ethyl}acetamide Starting compound: Preparation 81

Preparation 123: N-[2-(5-Amino-2-benzylbenzo[b]furan-3-yl)ethyl]-1cyclopropanecarboxamide Starting compound: Preparation 103

Preparation 124: N-[(6-Amino-3,4-dihydro-2H-3-chromenyl)methyl]acetamide

Starting compound: Preparation 82

Preparation 125: N-[(6-Amino-2-phenyl-2H-3-chromenyl)methyl]butanamide

Starting compound: Preparation 104

Preparation 126: N-[2-(6-Amino-2,3-dihydro-1,4-benzodioxin-5-yl)ethyl]acetamide

Starting compound: Preparation 87

Preparation 127: N-[(9-Amino-2,3-dihydro-1H-benzo[f]chromen-2-yl)methyl]-2-cyclopropylacetamide Starting compound: Preparation 88

Preparation 128: N-(4-Amino-2,3-dihydro-1H-2-phenalenyl)-N'-cyclopropylthiourea

Starting compound: Preparation 89

Preparation 129: N-[2-(7-Amino-3-phenyl-1-naphthyl)ethyl]acetamide

Starting compound: Preparation 106

Preparation 130: N-Cyclobutyl-6-amino-4,5-dihydro-3H-benzo[cd]isobenzofuran-4-carboxamide Starting compound: Preparation 90

Preparation 131: N-[2-(7-Amino-3-naphthyl-1-naphthyl)ethyl]heptanamide

Starting compound: Preparation 91

Preparation 132: N-[2-(5-Aminobenzo[b]furan-3-yl)ethyl]acetamide

Starting compound: Preparation 108

Preparation 133: N-[2-(7-Amino-1,2,3,4-tetrahydro-1-naphthyl)ethyl]acetamide

Starting compound: Preparation 107

Preparation 134: N-[2-(6-Amino-2,3-dihydro-1H-1-indenyl)ethyl]acetamide

Starting compound: Preparation 105

Preparations 135 to 145 are obtained by proceeding as in Preparation 1, starting from the appropriate substrate.

Preparation 135: N-[2-(7-Hydroxy-1-naphthyl)
ethyl]-2-furamide

Preparation 136: N-[2-(7-Hydroxy-1-naphthyl)ethyl]
benzamide

Preparation 137: N-[2-(7-Hydroxy-1-naphthyl)ethyl]
cyclopropanecarboxamide

Preparation 138: N-[2-(5-Hydroxy-1-benzofuran-3-
yl)ethyl]benzamide

Preparation 139: N-[2-(5-Hydroxy-1-benzofuran-3-
yl)ethyl]-2-furamide

Preparation 140: N-[2-(5-Hydroxy-1-benzofuran-3-
yl)ethyl]cyclopropanecarboxamide Preparation 141: N-[2-(5-Hydroxy-1-
benzothiophen-3-yl)ethyl]cyclopropanecarboxamide Preparation 142: N-[2-(5-Hydroxy-1H-pyrrolo[2,3-
b]pyridin-3-yl)ethyl]acetamide Preparation 143: N-[2-(5-Hydroxy-1H-pyrrolo[2,3-
b]pyridin-3-yl)ethyl]cyclopropanecarboxamide Preparation 144: N-[2-(5-Hydroxy-1H-pyrrolo[2,3-
b]pyridin-3-yl)ethyl]benzamide Preparation 145: N-[2-(5-Hydroxy-1H-pyrrolo[2,3-
b]pyridin-3-yl)ethyl]-2-furamide Preparation 146: N-[2-(5-Bromo-1H-pyrrolo[2,3-b]
pyridin-3-yl)ethyl]acetamide The procedure is as in Preparation 40, starting from the compound obtained in Preparation 142.

Preparation 147: N-[2-(5-Iodo-1H-pyrrolo[2,3-b]
pyridin-3-yl)ethyl]acetamide

The procedure is as in Preparation 73, starting from the compound obtained in Preparation 146.

Preparation 148: N-[2-(5-Amino-1H-pyrrolo[2,3-b]
pyridin-3-yl)ethyl]acetamide

The procedure is as in Preparation 109, starting from the compound obtained in Preparation 147.

Preparation 149: N-[2-(5-Bromo-1H-pyrrolo[2,3-b]
pyridin-3-yl)ethyl]-2-furamide

The procedure is as in Preparation 40, starting from the compound obtained in Preparation 145.

Preparation 150: N-[2-(5-Iodo-1H-pyrrolo[2,3-b]
pyridin-3-yl)ethyl]-2-furamide

The procedure is as in Preparation 73, starting from the compound obtained in Preparation 149.

Preparation 151: N-[2-(5-Amino-1H-pyrrolo[2,3-b]
pyridin-3-yl)ethyl]-2-furamide

The procedure is as in Preparation 109, starting from the compound obtained in Preparation 150.

Preparation 152: N-[2-(5-Bromo-1H-pyrrolo[2,3-b]
pyridin-3-yl)ethyl]benzamide

The procedure is as in Preparation 40, starting from the compound obtained in Preparation 144.

Preparation 153: N-[2-(5-Iodo-1H-pyrrolo[2,3-b]
pyridin-3-yl)ethyl]benzamide

The procedure is as in Preparation 73, starting from the compound obtained in Preparation 152.

Preparation 154: N-[2-(5-Amino-1H-pyrrolo[2,3-b]
pyridin-3-yl)ethyl]benzamide

The procedure is as in Preparation 109, starting from the compound obtained in Preparation 153.

Preparation 155: N-[2-(5-Bromo-1H-pyrrolo[2,3-b]
pyridin-3-yl)ethyl]cyclopropanecarboxamide The procedure is as in Preparation 40, starting from the compound obtained in Preparation 143.

Preparation 156: N-[2-(5-Iodo-1H-pyrrolo[2,3-b]
pyridin-3-yl)ethyl]cyclopropanecarboxamide The procedure is as in Preparation 73, starting from the compound obtained in Preparation 155.

Preparation 157: N-[2-(5-Amino-1H-pyrrolo[2,3-b]
pyridin-3-yl)ethyl]cyclopropanecarboxamide The procedure is as in Preparation 109, starting from the compound obtained in Preparation 156.

Preparation 158: N-[2-(5-Hydroxy-1H-pyrrolo[3,2-
b]pyridin-3-yl)ethyl]cyclopropanecarboxamide The procedure is as in Preparation 1.

Preparation 159: N-[2-(5-Bromo-1H-pyrrolo[3,2-b]
pyridin-3-yl)ethyl]cyclopropanecarboxamide The procedure is as in Preparation 40, starting from the compound obtained in Preparation 158.

Preparation 160: N-[2-(5-Iodo-1H-pyrrolo[3,2-b]
pyridin-3-yl)ethyl]cyclopropanecarboxamide The procedure is as in Preparation 73, starting from the compound obtained in Preparation 159.

Preparation 161: N-[2-(5-Amino-1H-pyrrolo[3,2-b]
pyridin-3-yl)ethyl]cyclopropanecarboxamide The procedure is as in Preparation 109, starting from the compound obtained in Preparation 160.

Preparation 162: N-[2-(5-Hydroxy-1H-pyrrolo[3,2-
b]pyridin-3-yl)ethyl]acetamide

The procedure is as in Preparation 1.

Preparation 163: N-[2-(5-Bromo-1H-pyrrolo[3,2-b]
pyridin-3-yl)ethyl]acetamide

The procedure is as in Preparation 40, starting from the compound obtained in Preparation 162.

Preparation 164: N-[2-(5-Iodo-1H-pyrrolo[3,2-b]
pyridin-3-yl)ethyl]acetamide

The procedure is as in Preparation 73, starting from the compound obtained in Preparation 163.

Preparation 165: N-[2-(5-Amino-1H-pyrrolo[3,2-b]
pyridin-3-yl)ethyl]acetamide

The procedure is as in Preparation 109, starting from the compound obtained in Preparation 164.

Preparation 166: N-[2-(5-Bromo-1-benzofuran-3-yl)ethyl]cyclopropanecarboxamide

The procedure is as in Preparation 40, starting from the compound obtained in Preparation 140.

Preparation 167: N-[2-(5-Iodo-1-benzofuran-3-yl)ethyl]cyclopropanecarboxamide

The procedure is as in Preparation 73, starting from the compound obtained in Preparation 166.

Preparation 168: N-[2-(5-Amino-1-benzofuran-3-yl)ethyl]cyclopropanecarboxamide

The procedure is as in Preparation 109, starting from the compound obtained in Preparation 167.

Preparation 169: N-[2-(5-Hydroxy-1-benzothiophen-3-yl)ethyl]benzamide

The procedure is as in Preparation 1.

Preparation 170: N-[2-(5-Bromo-1-benzothiophen-3-yl)ethyl]benzamide

The procedure is as in Preparation 40, starting from the compound obtained in Preparation 169.

Preparation 171: N-[2-(5-Iodo-1-benzothiophen-3-yl)ethyl]benzamide

The procedure is as in Preparation 73, starting from the compound obtained in Preparation 170.

Preparation 172: N-[2-(5-Amino-1-benzothiophen-3-yl)ethyl]benzamide

The procedure is as in Preparation 109, starting from the compound obtained in Preparation 171.

Preparation 173: N-[2-(7-Bromo-1-naphthyl)ethyl]-2-furamide

The procedure is as in Preparation 40, starting from the compound obtained in Preparation 135.

Preparation 174: N-[2-(7-Iodo-1-naphthyl)ethyl]-2-furamide

The procedure is as in Preparation 73, starting from the compound obtained in Preparation 173.

Preparation 175: N-[2-(5-Bromo-1-benzofuran-3-yl)ethyl]benzamide

The procedure is as in Preparation 40, starting from the compound obtained in Preparation 138.

Preparation 176: N-[2-(5-Iodo-1-benzofuran-3-yl)ethyl]benzamide

The procedure is as in Preparation 73, starting from the compound obtained in Preparation 176.

EXAMPLE 1

N-{8-[2-([2-Phenylacetyl]amino)ethyl]-2-naphthyl}butanamide

A solution of butanoic acid chloride (11 mmol) dissolved in ether (5 ml) is added dropwise to a solution of the product obtained in Preparation 109 (10 mmol) in ether (10 ml) and triethylamine (2 ml). The solution is stirred at ambient temperature until the amine has disappeared (monitored by TLC). At the end of the reaction, the organic phase is washed with water, dried, concentrated under reduced pressure and chromatographed on silica gel to yield the title product.

EXAMPLE 2

N-{2-[7-{[(Cyclohexylamino)carbonyl]amino}-1-naphthyl]ethyl}-2-phenylacetamide

A solution of cyclohexyl isocyanate in dichloromethane (5 ml) is added to a solution of the product obtained in Preparation 109 (10 mmol) in dichloromethane (10 ml). Stirring is carried out at ambient temperature until the starting amine has disappeared (monitored by TLC); the reaction mixture is then evaporated and concentrated under reduced pressure and is chromatographed on silica gel to yield the title product.

EXAMPLE 3

N-{2-[7-([Anilinocarbothioyl]amino)-1-naphthyl]ethyl}-2-phenylacetamide

The procedure is as in Example 2, but the cyclohexyl isocyanate is replaced by phenyl isothiocyanate to obtain the title product.

Is In Examples 4 to 16 the procedure is as in Example 1, starting from appropriate reactants.

EXAMPLE 4

N-(8-{2-[(2-Bromoacetyl)amino]ethyl}-2-naphthyl)-1-cyclohexanecarboxamide

Starting compound: Preparation 110

EXAMPLE 5

N-{1-Hexyl-8-[2-([2-phenylacetyl]amino)ethyl]-2-naphthyl}benzamide

Starting compound: Preparation 111

EXAMPLE 6

N-{6-Benzoyl-8-[2-{[(propylamino)carbonyl]amino}ethyl]-2-naphthyl}-2,2-dimethylpropanamide Starting compound: Preparation 115

EXAMPLE 7

N-{3-[4-(Methylamino)-4-oxobutyl]benzo[b]furan-5-yl}-3-butynamide

Starting compound: Preparation 119

EXAMPLE 8

N-{3-[2-(Acetylamino)ethyl]-2-[4-fluorobenzyl]-1-methyl-1H-pyrrolo[2,3-b]pyridin-5-yl}-3-phenyl-2-propenamide Starting compound: Preparation 122

EXAMPLE 9

N-{3-[(Acetylamino)methyl]-3,4-dihydro-2H-6-chromenyl}-2-phenylpropanamide

Starting compound: Preparation 124

EXAMPLE 10

N-{5-[2-(Acetylamino)ethyl]-2,3-dihydro-1,4-benzodioxin-6-yl}hexanamide

Starting compound: Preparation 126

EXAMPLE 11

N-{2-[([12-Cyclopropylacetyl]amino)methyl]-2,3-dihydro-1H-benzo[f]chromen-9-yl}-4-(trifluoromethyl)benzamide Starting compound: Preparation 127

EXAMPLE 12

N-{2-[([Cyclopropylamino]carbothioyl)amino]-2,3-dihydro-1H-4-phenalenyl}-4-ethoxybenzamide Starting compound: Preparation 128

EXAMPLE 13

N-{8-[2-(Acetylamino)ethyl]-6-phenyl-2-naphthyl}-1-cyclopentanecarboxamide

Starting compound: Preparation 129

EXAMPLE 14

N-Cyclobutyl-6-([2-cyclopropylacetyl)amino]-4,5-dihydro-3H-benzo[cd]-isobenzofuran-4-carboxamide Starting compound: Preparation 130

EXAMPLE 15

N-{8-[2-(Heptanoylamino)ethyl]-2,6-dinaphthyl}-2-butenamide

Starting compound: Preparation 131

EXAMPLE 16

N-{2-[6-(Acetylamino)-2,3-dihydro-1H-1-indenyl]ethyl}acetamide

Starting compound: Preparation 134

Examples 17 to 23 are obtained by proceeding as in Example 2, starting from appropriate reactants.

EXAMPLE 17

N-Cyclohexyl-4-{7-[(anilinocarbonyl)amino]-1-naphthyl}butanamide

Starting compound: Preparation 112

EXAMPLE 18

N-{(1-Methyl-2-[2-{[([morpholinomethyl]amino)carbonyl]amino}-1-naphthyl]ethyl}propanamide Starting compound: Preparation 114

EXAMPLE 19

N-{2-[7-{[(Benzylamino)carbonyl]amino}-3-(cyclopropylmethyl)-1-naphthyl]ethyl}acetamide Starting compound: Preparation 118

EXAMPLE 20

N-{2-[5-{[(Allylamino)carbonyl]amino}thieno[3,2-b]pyridin-3-yl]ethyl}acetamide

Starting compound: Preparation 120

EXAMPLE 21

N-{2-[2-Benzyl-5-{[(1-ethynylamino)carbonyl]amino}benzo[b]furan-3-yl]ethyl}-1-cyclopropanecarboxamide Starting compound: Preparation 123

EXAMPLE 22

N-{[6-{[([3-Methyl-2-butenyl]amino)carbonyl]amino}-2-phenyl-2H-3-chromenyl]methyl}butanamide Starting compound: Preparation 125

EXAMPLE 23

N-[2-(7-{[(Cyclohexylamino)carbonyl]amino}-3-phenyl-1-naphthyl)ethyl]acetamide

Starting compound: Preparation 129

In Examples 24 to 29 the procedure is as in Example 3, starting from appropriate substrates.

EXAMPLE 24

N-{2-[7-{[(Isobutylamino)carbothioyl]amino}-1-naphthyl]ethyl}-2-bromoacetamide

Starting compound: Preparation 110

EXAMPLE 25

N-{3-[7-{[([4-Methylbenzyl]amino)carbothioyl]amino}-1-naphthyl]propyl}acetamide

Starting compound: Preparation 113

EXAMPLE 26

N-Methyl-4-{5-[([1-ethynylamino]carbothioyl)amino]benzo[b]furan-3-yl}butanamide

Starting compound: Preparation 119

EXAMPLE 27

N-{2-[5-{[(Butylamino)carbothioyl]amino}-1H-3-indoly]ethyl}benzamide

Starting compound: Preparation 121

EXAMPLE 28

N-{[9-([Anilinocarbothioyl]amino)-2,3-dihydro-1H-benzo[f]chromen-2-yl]methyl}-2-cyclopropylacetamide Starting compound: Preparation 127

EXAMPLE 29

N-Cyclobutyl-6-{[([2,3-dimethyl-2-butenyl]amino)carbothioyl]amino}-4,5-dihydro-3H-benzo[cd]isobenzofuran-4-carboxamide Starting compound: Preparation 130

EXAMPLE 30

N-Ethyl-8-{2-[(2-phenylacetyl)amino]ethyl}-2-naphthamide

The procedure is as in Preparation 109, but instead of converting the acid chloride into an amine, it is treated with an amine to yield the title amide according to the procedure described below.

A solution of the product obtained in Step D of Preparation 109 (3.5 mmol) in ether (10 ml) is added, dropwise, to a solution of ethylamine (4 mmol) in ether (10 ml) and triethylamine (2 ml), maintained between 0 and 5° C. using an ice bath. Stirring is carried out at ambient temperature until the acid chloride has disappeared and the reaction mixture is then poured into a mixture of ice (10 g) and concentrated HCl (0.1 ml). The organic phase is washed with water, dried over magnesium sulphate, concentrated under reduced pressure and chromatographed on silica gel to yield the title product.

In Examples 31 to 50 the procedure is as in Example 30, but the ethylamine and the product of Step D of Preparation 109 are replaced by appropriate substrates.

EXAMPLE 31

N,N-Diethyl-8-{2-[2-[(cyclopropylmethyl)amino]-2-oxoethyl}-2-naphthamide

Starting compound: Preparation 74

EXAMPLE 32

N-Phenyl-8-(2-{methyl[(propylamino)carbonyl]amino}ethyl)-2-naphthamide

Starting compound: Preparation 75

EXAMPLE 33

N-(1-Ethynyl)-8-{2-[(cyclohexylcarbonyl)amino]ethyl}-2-naphthamide

Starting compound: Preparation 76

EXAMPLE 34

N-Benzyl-1-{2-[(2,2,2-trifloroacetyl)amino]ethyl}-2-naphthamide

Starting compound: Preparation 77

EXAMPLE 35

N-{2-[3-Benzoyl-7-(morpholinocarbonyl)-1-naphthyl]ethyl}-N'-propylurea

Starting compound: Preparation 78

EXAMPLE 36

N,N-Diphenyl-3-[3-(acetylamino)propyl]benzo[b]furan-5-carboxamide

Starting compound: Preparation 79

EXAMPLE 37

N-Isopropyl-N-(2-propynyl)-3-[(acetylamino)methyl]-2-benzylbenzo[b]thiophene-5-carboxamide Starting compound: Preparation 80

EXAMPLE 38

N,N-Diethyl-3-[2-(acetylamino)ethyl]-2-(4-fluorobenzyl)-1-methyl-1H-pyrrolo[2,3-b]pyridine-5-carboxamide Starting compound: Preparation 81

EXAMPLE 39

Ethyl 2-{[(4-{2-[(2-phenylacetyl)amino]ethyl}-3,4-dihydro-2H-6-chromenyl)carbonyl]amino}acetate Starting compound: Preparation 83

EXAMPLE 40

N-Cyclohexyl-N-(1-ethynyl)-4-[2-(acetylamino)ethyl]-6-thiochromancarboxamide

Starting compound: Preparation 85

EXAMPLE 41

N-Benzyl-3-(2-{[(propylamino)carbonyl]amino}ethyl-1,4-benzodioxin-6-carboxamide

Starting compound: Preparation 86

EXAMPLE 42

N-(3-Methyl-2-butenyl)-2-{[(2-cyclopropylacetyl)amino]methyl}-2,3,6,10b-tetrahydro-1H-benzo[f]chromene-8-carboxamide Starting compound: Preparation 88

EXAMPLE 43

N-[3-Phenyl-2-propenyl]-2-{[(cyclopropylamino)carbothioyl]amino)-2,3-dihydro-1H-4-phenalenecarboxamide Starting compound: Preparation 89

EXAMPLE 44

N-Cyclobutyl-N-trityl-4,5-dihydro-3H-benzo[cd]isobenzofuran-4,6-5 dicarboxamide

Starting compound: Preparation 90

EXAMPLE 45

Ethyl 2-[({8-[2-heptanoylamino)ethyl]-6-naphthyl-2-naphthyl}carbonyl)amino]acetate Starting compound: Preparation 91

EXAMPLE 46

N-(1-Ethynyl)-8-{2-[(2-bromoacetyl)amino]ethyl}-2-naphthamide

Starting compound: Preparation 94

EXAMPLE 47

N-Phenyl-1-hexyl-8-{2-[(2-phenylacetyl)amino]ethyl}-2-naphthamide

Starting compound: Preparation 95

EXAMPLE 48

Ethyl 2-({[8-[2-(acetylamino)ethyl]-6-(cyclopropylmethyl)-2-naphthyl]carbonyl}amino)acetate Starting compound: Preparation 99

EXAMPLE 49

N-(1-Ethynyl)-2-benzyl-3-{2-[(cyclopropylcarbonyl)amino]ethyl}benzo[b]furan-5-carboxamide Starting compound: Preparation 103

EXAMPLE 50

N-(1-Isopropyl-2-propynyl)-3-[(butynylamino) methyl]-2-phenyl-2H-6-chromenecarboxamide Starting compound: Preparation 104

EXAMPLE 51

N-Phenyl-8-(2-{methyl[(propylamino)carbothioyl] amino}ethyl)-2-naphthalenecarbothioamide The product obtained in Example 32 is treated with Lawesson's reagent to yield the title compound.

In Examples 52 to 57 the procedure is as in Example 51, taking the appropriate starting substrate.

EXAMPLE 52

N-Benzyl-1-{2-[(2,2,2-trifluoroethanethioyl)amino] ethyl}-2-naphthalenecarbothioamide Starting compound: Example 34

EXAMPLE 53

N,N-Diphenyl-3-[3-(ethanethioylamino)propyl] benzo[b]furan-5-carbothioamide

Starting compound: Example 36

EXAMPLE 54

N,N-Diethyl-3-[2-(ethanethioylamino)ethyl]-2-(4-fluorobenzyl)-1-methyl-1H-pyrrolo[2,3-b]pyridine-5-carbothioamide Starting compound: Example 38

EXAMPLE 55

N-Cyclohexyl-N-(1-ethynyl)-4-[2-(ethanethioylamino)ethyl]-6-thiochromancarbothioamide Starting compound: Example 40

EXAMPLE 56

N-(3-Methyl-2-butenyl)-2-{[(2-cyclopropylethanethioyl)amino]methyl}-2,3,6,10b-tetrahydro-1H-benzo[f]chromene-8-carbothioamide Starting compound: Example 42

EXAMPLE 57

N-[3-Phenyl-2-propenyl]-2-{[(cyclopropylamino) carbothioyl]amino}-2,3-dihydro-1H-4-phenalenecarbothioamide Starting compound: Example 43

In Examples 58 to 61 the procedure is as in Example 1, but the acid chloride is replaced by the corresponding halogenocarboxylate.

EXAMPLE 58

Methyl N-{3-[2-(acetylamino)ethyl]benzo[b]furan-5-yl}carbamate

Starting compound: Preparation 132
Melting point=138–140° C.

EXAMPLE 59

Ethyl N-(8-{2-[(2-bromoacetyl)amino]ethyl}-2-naphthyl)carbamate

Starting compound: Preparation 110

EXAMPLE 60

Methyl N-[8-[2-(acetylamino)ethyl]-6-phenyl-2-naphthyl}carbamate

Starting compound: Preparation 129

EXAMPLE 61

Hexyl N-{8-[2-(acetylamino)ethyl]-5,6,7,8-tetrahydro-2-naphthyl}carbamate

Starting compound: Preparation 133

EXAMPLE 62

N-[2-(5-Methoxycarbonylbenzo[b]furan-3-yl)ethyl] acetamide

Step A: 3-Acetyl-4-hydroxybenzoic acid 166 mmol of aluminium chloride are added slowly to 150 ml of nitrobenzene. 83 mmol of 4-acetylbenzoic acid are then added and heating is carried out at 120° C. for 2 hours. The mixture is hydrolysed using 1.2 liters of ice-cold water and the aqueous phase is acidified with 20 ml of concentrated HCl. Then, extraction with ethyl acetate and washing with aqueous 5% sodium carbonate solution are carried out. The aqueous phase is acidified with 6N HCl and the precipitate obtained is dried and recrystallised.

Melting point=120–121° C.

Step B: 3-(2-Bromoacetyl)-4-hydroxybenzoic acid

The compound obtained in Step A (32.2 mmol) is dissolved in glacial acetic acid (40 ml) and then 48.3 mmol of bromine are added. The mixture is heated at 80° C. for 2 hours and is then hydrolysed using ice-cold water. The precipitate obtained is filtered off, washed with water until a pH of 5–6 is obtained, and then dried and recrystallised.

Melting point=174–175° C.

Step C: Methyl 3-bromoacetyl-4-hydroxybenzoate

The compound obtained in Step B (27.4 mmol) is dissolved in 150 ml of MeOH, and 54.8 mmol of thionyl chloride are added dropwise in the cold state. The mixture is then stirred for 1 hour at ambient temperature and then for 2 hours at reflux. After evaporating off the methanol and the thionyl chloride, the oily residue is taken up in AcOEt, washed with water and then dried over $MgSO_4$. The solvent is evaporated off under reduced pressure and the solid obtained is recrystallised.

Melting point=93–94° C.

Step D: 5-(Methoxycarbonyl-3-benzo[b]furan-3-yl) acetonitrile

The compound obtained in Step C (15 mmol) is dissolved in 35 ml of acetone. 30 mmol of potassium carbonate are added and the mixture is stirred for 2 hours at ambient temperature. The precipitate formed is filtered off, washed with acetone and the filtrate is evaporated under reduced pressure. The benzofuranone formed is used directly in the following step: 22.5 mmol of NaH are introduced into a 250 ml round-bottomed two-necked flask which is placed in a bath of ice/salt and under a nitrogen atmosphere. 22.5 mmol of diethyl cyanophosphonate are added dropwise and the mixture is then stirred for 20 minutes. The benzofuranone previously obtained, in 140 ml of anhydrous THF, is added and the mixture is stirred for 2 hours at ambient temperature. After hydrolysing on a pile of ice and extracting with Et$_2$O, the organic phase is dried over MgSO$_4$ and the solvent is then evaporated off under reduced pressure. The title compound is purified by chromatography on a silica gel column (eluant: CH$_2$Cl$_2$), and is then recrystallised.

Melting point=125–126° C.

Step E: N-[2-(5-Methoxycarbonylbenzo[b]furan-3-yl)ethyl]acetamide

The 5-(methoxycarbonylbenzo[b]furan-3-yl)acetonitrile obtained in Step D (6.46 mmol) is dissolved in acetic anhydride (30 ml) in an autoclave, and 14.4 mmol of Raney nickel are added. After stirring overnight at 60° C. and under a hydrogen pressure of 60 bars, the catalyst is filtered off and washed with methanol. The filtrate is evaporated to dryness and the chestnut-coloured precipitate obtained is chromatographed on a silica gel column using ethyl acetate as eluant and is then recrystallised.

Melting point=121–122° C.

Elemental microanalysis:

|  | C | H | N |
|---|---|---|---|
| % calculated: | 64.36 | 5.78 | 5.36 |
| % found: | 64.14 | 5.81 | 5.28 |

EXAMPLE 63

Methyl 3-[2-(2-furoylamino)ethyl]-1-benzofuran-5-carboxylate

Step A: Methyl 3-(2-aminoethyl)-1-benzofuran-5-carboxylate hydrochloride 6.57 mmol of the compound obtained in Step D of Example 62 are dissolved in 150 ml of methanol. The solution is introduced into an autoclave and 28.8 mmol of Raney nickel are added. The solution is saturated with ammonia, and then hydrogen is introduced until a pressure of 60 bars is obtained. The solution is stirred for 4 hours at a temperature of 60° C. After cooling, the catalyst is filtered off, and the methanol is then evaporated off. The residue is purified by chromatography on a silica gel column using a mixture of dichloromethane/methanol (7/3) and then methanol as eluant. The amine obtained is dissolved in absolute ethanol. Stirring is carried out in an ice bath and gaseous hydrogen chloride is bubbled through. The hydrochloride obtained is filtered off under suction and dried in a desiccator.

Melting point=210–211° C.

Step B: Methyl 3-[2-(2-furoylamino)ethyl]-1-benzofuran-5-carboxylate 1 mmol of the compound obtained in Step A is introduced into 30 ml of anhydrous CH$_2$Cl$_2$. The temperature is lowered with the aid of an ice bath, and 1.5 mmol of triethylamine and then 1.5 mmol of 2-furoic acid chloride are added dropwise in succession. The mixture is stirred for 20 minutes, and the organic phase is then washed with water, dried over MgSO$_4$ and evaporated. The residue is purified by chromatography on a silica gel column and the title product is recrystallised.

Melting point=116–118° C.

Elemental microanalysis:

|  | C | H | N |
|---|---|---|---|
| % calculated: | 65.17 | 4.82 | 4.47 |
| % found: | 64.80 | 4.84 | 4.50 |

EXAMPLE 64

Methyl 3-{2-[(cyclopentylcarbonyl)amino]ethyl}-1-benzofuran-5-carboxylate

The procedure is as in Example 63.
Melting point=122–123° C.

EXAMPLE 65

Methyl 3-{2-[(cyclopropylcarbonyl)amino]ethyl}-1-benzofuran-5-carboxylate

The procedure is as in Example 63.
Melting point=154–155° C.

EXAMPLE 66

Methyl 3-[2-(3-butenoylamino)ethyl]-1-benzofuran-5-carboxylate

Vinylacetic acid (1 mmol), 1-ethyl-3-(3-dimethylaminopropyl-3-ethyl)carbodiimide hydrochloride (E.D.C.) (1.1 mmol) and hydroxybenzotriazole (HOBT) (1.1 mmol) are dissolved in dichloromethane (30 ml) in a flask cooled to −20° C. After 30 minutes, the compound obtained in Step A of Example 63 (1 mmol), dissolved in dichloromethane (20 ml), is added dropwise. The reaction mixture is stirred for 30 minutes at −20° C. and then overnight at ambient temperature. The dichloromethane is evaporated off and the residue is purified by chromatography on a silica gel column.

Melting point=98–100° C.

EXAMPLE 67

3-[2-(Acetylamino)ethyl]-1-benzofuran-5-carboxamide

The ester (0.1 mol) obtained in Example 62, dissolved in an aqueous 20% ammonium hydroxide solution (50 ml), is heated for 5 hours at 60° C. The reaction mixture is cooled and is then evaporated to dryness. The residue obtained is purified by chromatography on a silica gel column.

Melting point=206–208° C.

Elemental microanalysis:

|  | C | H | N |
|---|---|---|---|
| % calculated: | 63.40 | 5.73 | 11.38 |
| % found: | 63.23 | 5.89 | 11.17 |

EXAMPLE 68

3-{2-[(Cyclopropylcarbonyl)amino]ethyl}-1-benzofuran-5-carboxamide

The same procedure is used as in Example 67.
Melting point=209–210° C.

EXAMPLE 69

3-[2-(2-Furoylamino)ethyl]-1-benzofuran-5-carboxamide

The same procedure is used as in Example 67.
Melting point=110–112° C.
Elemental microanalysis:

|  | C | H | N |
|---|---|---|---|
| % calculated: | 64.42 | 4.73 | 9.39 |
| % found: | 64.23 | 4.98 | 9.97 |

EXAMPLE 70

3-{2-[(Cyclopropylcarbonyl)amino]ethyl}-N-methyl-1-benzofuran-5-carboxamide

To the ester obtained in Example 62 (1 mmol), dissolved in methanol (40 ml) in the hot state, there is added an aqueous 40% methylamine solution (1.6 mmol), and the mixture is refluxed for 2 hours. The reaction mixture is then cooled and the methanol is subsequently evaporated off. The aqueous phase is extracted with ethyl acetate, the organic phase is dried over magnesium sulphate and the solvent is evaporated off. The residue is purified by chromatography on a silica gel column.
Melting point=188–189° C.
Elemental microanalysis:

|  | C | H | N |
|---|---|---|---|
| % calculated: | 67.11 | 6.34 | 9.78 |
| % found: | 67.00 | 6.34 | 9.77 |

EXAMPLE 71

3-[2-(Acetylamino)ethyl]-N-methyl-1-benzofuran-5-carboxamide

The same procedure is used as in Example 70.
Melting point 158–159° C.
Elemental microanalysis:

|  | C | H | N |
|---|---|---|---|
| % calculated: | 64.59 | 6.20 | 10.76 |
| % found: | 64.27 | 6.13 | 10.44 |

EXAMPLE 72

3-{2-[(Cyclopentylcarbonyl)amino]ethyl}-N-methyl-1-benzofuran-5-carboxamide

The same procedure is used as in Example 70.
Melting point=170–171° C.

EXAMPLE 73

3-[2-(Benzoylamino)ethyl]-N-methyl-1-benzofuran-5-carboxamide

The same procedure is used as in Example 70.

EXAMPLE 74

N-{3-[2-(Acetylamino)ethyl]-1-benzofuran-5-yl}-2,2,2-trifluoroacetamide

Step A: 3-[2-(Acetylamino)ethyl]-1-benzofuran-5-carboxylic acid

To the ester obtained in Example 62 (2 mmol), dissolved in methanol (90 ml), there is added aqueous 30% sodium hydroxide solution (30 ml), and the mixture is stirred overnight. After evaporating off the methanol, the temperature of the reaction mixture is lowered with the aid of an ice bath and the mixture is acidified with hydrochloric acid solution (6N). The aqueous phase is extracted with ethyl acetate, and the organic phase is dried over magnesium sulphate and then evaporated to dryness. The residue obtained is recrystallised.
Melting point=210–211° C.

Step B: 3-[2-(Acetylamino)ethyl]-1-benzofuran-5-carbonyl azide

The acid (1 mmol) obtained in Step A is dissolved in acetone. The temperature of the reaction mixture is lowered with the aid of an ice bath, and triethylamine (1.5 mmol) and then ethyl chloroformate (1.5 mmol) are added. After stirring for 15 minutes, sodium azide (1.5 mmol), previously dissolved in water (1 ml of water per 400 mg of sodium azide), is added and stirring is again carried out for 10 minutes. The mixture is extracted with ethyl acetate, and the organic phase is then washed with water, dried over magnesium sulphate and evaporated to dryness. The azide obtained is used, without additional purification, in the following Step.

Step C: N-{3-[2-(Acetylamino)ethyl]-1-benzofuran-5-yl}-2,2,2-trifluoroacetamide

To the azide obtained in Step B (460 mg, 1.68 mmol), dissolved in dichloromethane, there is added trifluoroacetic acid (1.82 ml, 2.35 mmol) and stirring is carried out overnight. The reaction mixture is washed with water and then with aqueous 10% sodium hydrogen carbonate solution.

The organic phase is dried over magnesium sulphate and then evaporated. The residue obtained is purified by chromatography on a silica gel column using ethyl acetate as eluant.
Melting point=152–154° C.

EXAMPLE 75

Methyl 3-{2-[(cyclopropylcarbonyl)amino]ethyl}-1-benzofuran-5-yl-carbamate

The azide obtained in Step B of Example 74 (1 mmol) is heated at 80° C. overnight and 5 ml of MeOH and 5 ml of toluene are added. After evaporating off the solvent, the residue obtained is purified by chromatography on a silica gel column.
Melting point=153–155° C.
Elemental microanalysis:

|  | C | H | N |
|---|---|---|---|
| % calculated: | 63.56 | 6.00 | 9.27 |
| % found: | 63.27 | 6.02 | 9.14 |

EXAMPLE 76 tert-Butyl 3-[2-(acetylamino)ethyl]-1-benzofuran-5-yl-carbamate

The procedure is as in Examples 74 and 75.
Melting point=146–148° C.
Elemental microanalysis:

|  | C | H | N |
|---|---|---|---|
| % calculated: | 64.12 | 6.97 | 8.79 |
| % found: | 64.03 | 6.58 | 8.67 |

EXAMPLE 77 tert-Butyl 3-[2-(acetylamino)ethyl]-1-benzofuran-5-yl-(methyl)carbamate

To 1.98 mmol of the carbamate obtained in Example 76, dissolved in dimethylformamide, there are added, in the cold state, 2.18 mmol of sodium hydride, and stirring is carried out for 2 hours at ambient temperature. 2.37 mmol of methyl iodide are added to the mixture and stirring is carried out for 4 hours at ambient temperature. The reaction mixture is hydrolysed, extracted with ethyl acetate, and the organic phase is then washed with water and dried over magnesium sulphate. The residue is recrystallised.

EXAMPLE 78

Methyl 3-[2-(benzoylamino)ethyl]-1-benzofuran-5-yl-carbamate

The procedure is as in Examples 74 and 75.

EXAMPLE 79

Methyl 3-[2-(isobutyrylamino)ethyl]-1-benzofuran-5-yl-carbamate

The procedure is as in Examples 74 and 75.

EXAMPLE 80

N-{2-[7-(Aminosulphonyl)-1-naphthyl]ethyl}acetamide

Step A: N-{2-[7-(Benzylthio)-1-naphthyl]ethyl}acetamide 4.4 mmol of the compound obtained in Preparation 1 are dissolved in 20 ml of anhydrous $CH_2Cl_2$ and placed under a current of nitrogen. 6.5 mmol of benzylthiol are added dropwise using a syringe and then 8.8 mmol of triflic acid are added, before the mixture is refluxed for 24 hours. After cooling, hydrolysis is carried out using 10% $Na_2CO_3$ solution. The organic phase is washed with 10% sodium hydroxide solution and then with water until the washing waters are neutral, and is then dried and evaporated. The residue is taken up in petroleum ether and recrystallised from a toluene/cyclohexane mixture.

Melting point=80–83° C.

Step B: 8-[2-(Acetylamino)ethyl]-2-naphthalenesulphonyl chloride 3 mmol of the compound obtained in Step A are crushed in a mortar, together with 13.1 mmol of iodosobenzene and 107 g of silica/HCl, with the aid of a pestle. Dichloromethane is added and the silica is filtered off and washed several times with $CH_2Cl_2$. The filtrate obtained is evaporated and the residue is taken up in petroleum ether and then filtered.

Step C: N-{2-[7-(Aminosulphonyl)-1-naphthyl]ethyl}acetamide 0.8 mmol of the compound obtained in Step B is dissolved in 10 ml of $CH_2Cl_2$ and then 1.2 mmol of triethylamine are added. The mixture is cooled with the aid of an ice bath and 1.2 mmol of ammonium hydroxide solution are added dropwise. After stirring for 2 hours, the mixture is evaporated and the residue obtained is recrystallised.

Melting point=194–196° C.

EXAMPLE 81

N-(2-{7-[(Methylamino)sulphonyl]-1-naphthyl}ethyl)acetamide

The procedure is as in Example 80, but the ammonium hydroxide in Step C is replaced by methylamine.

Melting point=155–156° C.

By proceeding as in Example 80, but replacing, in Step A, the compound of Preparation 1 by the appropriate substrate, and, in Step C, the ammonium hydroxide by the appropriate amine, Examples 82 to 84 are obtained:

EXAMPLE 82

N-(2-{7-[(Methylamino)sulphonyl]-1-naphthyl}ethyl)-2-furamide

Starting compound: Preparation 135

EXAMPLE 83

N-(2-{7-[(Ethylamino)sulphonyl]-1-naphthyl}ethyl)benzamide

Starting compound: Preparation 136

EXAMPLE 84

N-(2-{7-[(Methylamino)sulphonyl]-1-naphthyl}ethyl)cyclopropanecarboxamide

Starting compound: Preparation 137

EXAMPLE 85

N-(3-{5-[(Methylamino)sulphonyl]-1-benzofuran-3-yl}propyl)acetamide

Starting compound: Preparation 16

EXAMPLE 86

N-(2-{5-[(Propylamino)sulphonyl]-1-benzofuran-3-yl}ethyl)acetamide

Starting compound: Preparation 18

EXAMPLE 87

N-(2-{5-[(Cyclopropylamino)sulphonyl]-1-benzofuran-3-yl}ethyl)benzamide

Starting compound: Preparation 138

EXAMPLE 88

N-(2-{5-[(Methylamino)sulphonyl]-1-benzofuran-3-yl}ethyl)-2-furamide

Starting compound: Preparation 139

EXAMPLE 89

N-(2-{5-[(Hexylamino)sulphonyl]-1-benzofuran-3-yl}ethyl)cyclopropanecarboxamide

Starting compound: Preparation 140

EXAMPLE 90

N-(2-{5-[(Methylamino)sulphonyl]-1-benzofuran-3-yl}ethyl)cyclopropanecarboxamide Starting compound: Preparation 140

EXAMPLE 91

N-(2-{2-Benzyl-5-[(methylamino)sulphonyl]-1-benzothiophen-3-yl}ethyl)acetamide

Starting compound: Preparation 19

EXAMPLE 92

N-(2-{5-[(Isopropylamino)sulphonyl]-1-benzothiophen-3-yl}ethyl)cyclopropanecarboxamide Starting compound: Preparation 141

EXAMPLE 93

N-(2-{5-[(Methylamino)sulphonyl]1H-pyrrolo[2,3-b]pyridin-3-yl}ethyl)acetamide

Starting compound: Preparation 142

EXAMPLE 94

N-(2-{5-[(Methylamino)sulphonyl]1H-pyrrolo[2,3-b]pyridin-3-yl}ethyl)-cyclopropanecarboxamide Starting compound: Preparation 143

EXAMPLE 95

N-(2-{5-[(Methylamino)sulphonyl]1H-pyrrolo[2,3-b]pyridin-3-yl}ethyl)benzamide

Starting compound: Preparation 144

EXAMPLE 96

N-(2-{5-[(Methylamino)sulphonyl]1H-pyrrolo[2,3-b]-pyridin-3-yl}ethyl)-2-furamide Starting compound: Preparation 145

Examples 97 to 105 are obtained by proceeding as in Example 1, but replacing the acid chloride by the corresponding halogenocarboxylate.

EXAMPLE 97

Methyl 5-[(acetylamino)methyl]-2,3-dihydro-1,4-benzodioxin-6-yl-carbamate

Starting compound: Preparation 126

EXAMPLE 98

Methyl 3-[(acetylamino)methyl]-3,4-dihydro-2H-chromen-6-yl-carbamate

Starting compound: Preparation 124

EXAMPLE 99

Ethyl 3-[2-(acetylamino)ethyl]-2,3-dihydro-1H-inden-5-yl-carbamate

Starting compound: Preparation 134

EXAMPLE 100

Methyl 3-[2-(acetylamino)ethyl]-1H-pyrrolo[2,3-b]pyridin-5-yl-carbamate

Starting compound: Preparation 148

EXAMPLE 101

Methyl 3-[2-(2-furoylamino)ethyl]-1H-pyrrolo[2,3-b]pyridin-5-yl-carbamate

Starting compound: Preparation 151

EXAMPLE 102

Methyl 3-[2-(benzoylamino)ethyl]-1H-pyrrolo[2,3-b]pyridin-5-yl-carbamate

Starting compound: Preparation 154

EXAMPLE 103

Methyl 3-{2-[(cyclopropylcarbonyl)amino]ethyl}-1H-pyrrolo[2,3-b]pyridin-5-yl-carbamate Starting compound: Preparation 157

EXAMPLE 104

Methyl 3-{2-[(cyclopropylcarbonyl)amino]ethyl}-1H-pyrrolo[3,2b]pyridin-5-yl-carbamate Starting compound: Preparation 161

EXAMPLE 105

Ethyl 3-[2-(acetylamino)ethyl]-1H-pyrrolo[3,2b]pyridin-5-yl-carbamate

Starting compound: Preparation 165

Examples 106 to 108 are obtained by proceeding as in Example 1, starting from the appropriate substrate.

EXAMPLE 106

N-{8-[2-(Acetylamino)ethyl]-2-naphthyl}acetamide

Starting compound: Preparation 117

EXAMPLE 107

N-{2-[5-(Acetylamino)-1-benzofuran-3-yl]ethyl}cyclopropanecarboxamide

Starting compound: Preparation 168

EXAMPLE 108

N-{2-[5-(Acetylamino)-1-benzothiophen-3-yl]ethyl}benzamide

Starting compound: Preparation 172

Examples 109 to 112 are obtained by proceeding as in Preparation 109, condensing the appropriate amine with the intermediate acid chloride.

EXAMPLE 109

3-[2-(Acetylamino)ethyl]-N-methyl-1H-pyrrolo[2,3-b]pyridine-5-carboxamide

Starting compound: Preparation 147

EXAMPLE 110

N-(2-{7-[(Methylamino)carbonyl]-1-naphthyl}ethyl)-2-furamide

Starting compound: Preparation 174

EXAMPLE 111

3-{2-[(Cyclopropylcarbonyl)amino]ethyl}-N-ethyl-1-benzofuran-5-carboxamide

Starting compound: Preparation 167

EXAMPLE 112

3-[2-(Benzoylamino)ethyl]-N-ethyl-1-benzofuran-5-carboxamide

Starting compound: Preparation 176

EXAMPLE 113

N-{8-[2-(Acetylamino)ethyl]-5,6,7,8-tetrahydro-2-naphthyl}acetamide

Step A: 7-Nitro-3,4-dihydro-1(2H)-naphthalenone 7 mmol of 1-oxo-1,2,3,4-tetrahydronaphthalene and 5 ml of concentrated sulphuric acid are cooled in a freezer for 30 minutes. The reaction mixture is then placed in a bath of alcohol at −15° C. on a cooling plate. A sulphonitric mixture (1.1 ml of sulphuric acid and 0.73 ml of nitric acid) is prepared and brought to the temperature of the reaction mixture before being added dropwise, avoiding any drastic heating of the mixture. Stirring is carried out for 15 minutes and then hydrolysis on a pile of ice is carried out. The pale yellow precipitate obtained is washed with water until the washing waters have a neutral pH and is then dried in a desiccator and purified on a silica gel column.

Melting point=103.7–104.3° C.

Step B: 2-[7-Nitro-3,4-dihydro-1(2H)-naphthalenylidene]acetonitrile

Using a 50 ml two-necked flask under a current of nitrogen and placed in a bath of alcohol at −15° C., 0.32 g of sodium hydride is added in portions to 40 ml of THF, with magnetic stirring, and then 1.4 g of diethyl cyanomethylphosphonate in 10 ml of THF are added dropwise. After stirring for half an hour, when the mixture is highly homogeneous, the flask is plunged into a medium at −78° C. (cryostat), and 1 g of the compound obtained in Step A, dissolved in 20 ml of THF, is added dropwise. Stirring under a current of nitrogen is carried out for 2 hours. The reaction mixture is then brought to ambient temperature, hydrolysed on ice and precipitated. After filtering under suction and washing with water until the washing waters have a neutral pH, extraction with 3 volumes of ether is carried out. The organic phases are washed with 3 volumes of water and then dried. The grey solid obtained is decolorised on carbon.

Melting point=98.1–98.5° C.

Step C: N-{8-[2-(Acetylamino)ethyl]-5,6,7,8-tetrahydro-2-naphthyl}acetamide 9 mmol of the compound obtained in Step B are dissolved in acetic anhydride (100 ml) and then a small spatula of sodium acetate is added. The mixture is introduced into an autoclave, Raney nickel is added and autoclaving under a pressure of 40 bars is carried out for 6 hours, with stirring at 50–60° C. The mixture is filtered and is rinsed with alcohol at 95° C.; the solvent is then evaporated off. Hydrolysis is carried out using 100 ml of distilled water and extraction with 3 volumes of dichloromethane is carried out. The organic phase is washed with 2 volumes of water, dried over magnesium sulphate, filtered and evaporated. Rinsing with an ether/dichloromethane mixture and trituration in ether are carried out. The light-beige solid obtained is recrystallised.

Melting point=127.7–128.7° C.

Elemental microanalysis

|              | C     | H    | N     |
|--------------|-------|------|-------|
| % calculated: | 70.04 | 8.08 | 10.21 |
| % found:     | 69.74 | 8.14 | 10.43 |

EXAMPLE 114

Methyl 8-[2-(acetylamino)ethyl]-2-naphthylcarbamate

The procedure is as in Example 97.

Starting compound: Preparation 117

EXAMPLE 115

N[2-(1,3-Dioxo-1,2,3,4-tetrahydrobenzo[f]quinolin-10-yl)ethyl]-2-phenylacetamide A solution of the product obtained in Preparation 109 (10 mmol) in ether (160 ml) is added very slowly, using a dropper, to a solution of malonyl dichloride (40 mmol) in ether (40 ml) and triethylamine (2 ml). At the end of the reaction, the reaction mixture is concentrated under reduced pressure. The residue is dried using a vane pump and then taken up in ether. The organic phase is washed with water, dried over magnesium sulphate, concentrated under reduced pressure and then dried using a vane pump. The residue is then taken up in 100 ml of 1,1,2,2-tetrachloroethane. The resulting solution is then added dropwise to a solution of aluminium chloride (30 mmol) in 50 ml of the same solvent under nitrogen. The mixture is heated at 60° C. until the reaction has ceased; the reaction mixture is then poured into a mixture of ice (20 g) and concentrated HCl (1 ml) and is stirred for one hour. The aqueous phase is extracted twice with chloroform and then the combined organic phases are dried over magnesium sulphate and concentrated under reduced pressure. The residue is chromatographed on silica gel to yield the title product.

In Examples 116 to 120 the procedure is as in Example 115, starting from appropriate substrates.

EXAMPLE 116

N-Cyclohexyl-4-(1,3-dioxo-1,2,3,4-tetrahydrobenzo[f]quinolin-10-yl)-butanamide

Starting compound: Preparation 112

EXAMPLE 117

N-[2-(7-Benzoyl-1,2-dioxo-2,3-dihydro-1H-benzolelindol-9-yl)ethyl]-N'-propylurea Starting compound: Preparation 115

EXAMPLE 118

N-Methyl-4-(7,9-dioxo-6,7,8,9-tetrahydrofuro[3,2-f]quinolin-1-yl)butanamide

Starting compound: Preparation 119

EXAMPLE 119

N-{2-[2-(4-Fluorobenzyl)-3-methyl-7,8-dioxo-3,6,7,8-tetrahydrodipyrrolo[2,3-b:3,2-d]pyridin-1-yl]ethyl}acetamide Starting compound: Preparation 122

EXAMPLE 120

N-[(8,10-Dioxo-2,3,7,8,9,10-hexahydro-1H-pyrano
[3,2-f]quinolin-2-yl)methyl]acetamide Starting compound: Preparation 124

EXAMPLE 121

N-[2-(3-Oxo-1,2,3,4-tetrahydrobenzo[f]quinolin-10-
yl)ethyl]-2-phenylacetamide

The product of Example 115 (3 mmol) is dissolved in acetic acid (70 ml). After several purges with argon, 10% palladium-on-carbon (600 mg) is added and the mixture is placed under a hydrogen atmosphere. Stirring is carried out at ambient temperature until the end of the reaction (monitored by TLC) and the palladium is filtered off over Celite. The acetic acid is evaporated off to dryness and the residue is chromatographed on silica gel to yield the title product.

In Examples 122 to 126 the procedure is as in Example 121, starting from appropriate substrates.

EXAMPLE 122

N-Cyclohexyl-4-(3-oxo-1,2,3,4-tetrahydrobenzo[f]
quinolin-10-yl)butanamide

Starting compound: Example 116

EXAMPLE 123

N-[2-(7-Benzoyl-2-oxo-2,3-dihydro-1H-benzo[e]
indol-9-yl)ethyl]-N'-propylurea

Starting compound: Example 117

EXAMPLE 124

N-Methyl-4-(9-oxo-6,7,8,9-tetrahydrofuro[3,2-f]
quinolin-1-yl)butanamide

Starting compound: Example 118

EXAMPLE 125

N-{2-[2-(4-Fluorobenzyl)-3-methyl-8-oxo-3,6,7,8-
tetrahydropyrrolo[2,3-b:3,2-d]pyridin-1-yl]
ethyl}acetamide Starting compound: Example 119

EXAMPLE 126

N-[(8-Oxo-2,3,7,8,9,10-hexahydro-1H-pyrano[3,2-f]
quinolin-2-yl)methyl]acetamide Starting compound: Example 120

EXAMPLE 127

N-[2-(4-Oxo-3,4-dihydrobenzo[f]isoquinolin-10-yl)
ethyl]-1-cyclohexanecarboxamide The product of Example 33 (10 mmol) and triethylene glycol are introduced into a two-necked flask. Heating is carried out at 160–170° C., under nitrogen and with stirring, for five hours. The reaction mixture is poured into ice-cold water and is extracted with ethyl acetate. The organic phase is washed with water and dried over calcium chloride. After filtration, the organic phase is concentrated under reduced pressure. The residue is chromatographed on silica gel to yield the title product.

In Examples 128 to 132, the procedure is as in Example 127, starting from appropriate substrates.

EXAMPLE 128

N-[2-(2-Benzyl-7-isopropyl-6-oxo-6,7-
dihydrothieno[3,2-f]isoquinolin-1-yl)ethyl]
acetamide Starting compound: Example 37

EXAMPLE 129

N-[2-(3-Cyclohexyl-4-oxo-3,8,9,10-tetrahydro-4H-
thiopyrano[3,2-f]isoquinolin-10-yl)ethyl]acetamide Starting compound: Example 40

EXAMPLE 130

N-[2-(4-Oxo-3,4-dihydrobenzo[f]isoquinolin-10-yl)
ethyl]-2-bromoacetamide

Starting compound: Example 46

EXAMPLE 131

N-[2-(2-Benzyl-6-oxo-6,7-dihydrofuro[3,2-f]
isoquinolin-1-yl)ethyl]-1-cyclopropanecarboxamide Starting compound: Example 49

EXAMPLE 132

N-[(9-Isopropyl-7-oxo-3-phenyl-3,7,8,9-
tetrahydrochromeno[6,5-c]azepin-2-yl)methyl]
butanamide Starting compound: Example 50

EXAMPLE 133

N-[2-(1,4-Dioxo-1,3,4,8,9,10-hexahydro-2H-pyrano
[3,2-f]isoquinolin-10-yl)ethyl]-2-phenylacetamide Step A: 2-{[(4-{2-[(2-Phenylacetyl)amino]ethyl}-3,4-dihydro-2H-chromen-6-yl)carbonyl]amino}acetic acid A 0.5N aqueous solution of $K_2CO_3$ (10 ml) is added to the product obtained in Example 39 (4 mmol) dissolved in methanol (10 ml). When the reaction has ceased, the solution is acidified to pH 6–7 using 1N hydrochloric acid solution. The reaction mixture is extracted with dichloromethane. The organic phase is washed with water, dried over magnesium sulphate and concentrated under reduced pressure. The residue is chromatographed on silica gel to yield the title product.

Step B: 2-{[(4-{2-[(2-Phenylacetyl)amino]ethyl}-3,4-dihydro-2H-chromen-6yl)carbonyl]amino}acetyl chloride The product obtained in Step A (3 mmol), dissolved in thionyl chloride, is stirred at 60° C. under a current of nitrogen for one hour. The thionyl chloride is evaporated off under reduced pressure and the residue is dried with the aid of a vane pump to yield the title product.

Step C: N-[2-(1,4-Dioxo-1,3,4,8,9,10-hexahydro-2H-pyrano[3,2-f]isoquinolin-10-yl)ethyl]-2-phenylacetamide The product obtained in Step B (3 mmol), dissolved in 1,1,2,2-tetrachloroethane (30 ml), is added dropwise to a solution of aluminium chloride (10 mmol) in the same solvent (20 ml) under nitrogen. The reaction mixture is heated at 60° C., with stirring, until the reaction has ceased. The solution is then poured into a mixture of ice (10 g)/concentrated HCl (0.3 ml) and stirring is carried out for one hour. The aqueous phase is extracted twice with chloroform; the combined organic phases are then dried over magnesium sulphate and concentrated under reduced pressure. The residue is chromatographed on silica gel to yield the title product.

In Examples 134 to 135 the procedure is as in Example 133, starting from appropriate reactants.

EXAMPLE 134

N-[2-(1,4-Dioxo-8-naphthyl-1,2,3,4-tetrahydro[f] isoquinolin-10-yl)ethyl]heptanamide Starting compound: Example 45

EXAMPLE 135

N-{2-[8-(Cyclopropylmethyl)-1,4-dioxo-1,2,3,4-tetrahydrobenzo[f]isoquinolin-10-yl]ethyl}acetamide Starting compound: Example 48

In Examples 136 to 138 the procedure is as in Example 122, starting from appropriate substrates.

EXAMPLE 136

N-[2-(4-Oxo-1,3,4,8,9,10-hexahydro-2H-pyrano[3,2-f]isoquinolin-10-yl)ethyl]-2-phenylacetamide Starting compound: Example 133

EXAMPLE 137

N-[2-(4-Oxo-8-naphthyl-1,2,3,4-tetrahydrobenzo[f] isoquinolin-10-yl)ethyl]heptanamide Starting compound: Example 134

EXAMPLE 138

N-{2-[8-(Cyclopropylmethyl)-4-oxo-1,2,3,4-tetrahydrobenzo [f]isoquinolin-10-yl] ethyl}acetamide Starting compound: Example 35

EXAMPLE 139

N-[2-(4-Thioxo-3,4-dihydrobenzo[f]isoquinolin-10-yl)ethyl]-1-cyclohexanecarbothioamide The product obtained in Example 127 is treated with Lawesson's reagent to yield the title compound. Examples 140 to 142 are obtained by proceeding as in Example 139.

EXAMPLE 140

N-[2-(3-Cyclohexyl-4-thioxo-3,8,9,10-tetrahydro-4H-thiopyrano[3,2-f]isoquinolin-10-yl)ethyl] acetamide Starting compound: Example 129

EXAMPLE 141

N-[2-(1,4-Dithioxo-1,3,4,8,9,10-hexahydro-2H-pyrano[3,2-f]isoquinolin-10-yl)ethyl]-2-phenylethanethioamide Starting compound: Example 133

EXAMPLE 142

N-{2-[8-(Cyclopropylmethyl)-4-thioxo-1,2,3,4-tetrahydrobenzo[f]isoquinolin-10-yl] ethyl}ethanethioamide Starting compound: Example 138

EXAMPLE 143

N-Cyclohexyl-4-(1-hydroxy-3-oxo-1,2,3,4-tetrahydrobenzo[f]quinolin-10-yl)butanamide A solution of the product obtained in Example 116 (2 mmol) dissolved in methanol (10 ml) is added dropwise to a suspension of sodium hydride (2.2 mmol) in methanol (50 ml) at −40° C. Stirring is carried out until the starting compound has completely disappeared (about 3 hours). At the end of the reaction, the solution is poured into water (30 ml). The reaction mixture is concentrated under reduced pressure to a volume of about 30 ml and is then extracted with ethyl acetate. The aqueous phase is washed with water, dried over magnesium sulphate and concentrated under reduced pressure. The residue is chromatographed on silica gel to yield the title product.

In Examples 144 and 145, the procedure is as in Example 143.

EXAMPLE 144

N-[(10-Hydroxy-8-oxo-2,3,7,8,9,10-hexahydro-1H-pyrano[3,2-f]quinolin-2-yl)methyl]acetamide Starting compound: Example 120

EXAMPLE 145

N-[2-(1-Hydroxy-4-methyl-1,2,3,4-tetrahydrobenzo [f]quinolin-10-yl)ethyl]-2-phenylacetamide Starting compound: Example 133

EXAMPLE 146

Methyl 3-[2-(2-furoylamino)ethyl]-1-benzofuran-5-yl-carbamate

The procedure is as in Examples 74 and 75.

EXAMPLE 147

Methyl 3-{2-[(cyclopentylcarbonyl)amino]ethyl}-1-benzofuran-5-yl-carbamate

The procedure is as in Examples 74 and 75.

EXAMPLE 148

Methyl 3-[2-(benzoylamino)ethyl]-1-benzofuran-5-carboxylate

The procedure is as in Example 63.

EXAMPLE 149

Methyl 3-[2-(isobutylamino)ethyl]-1-benzofuran-5-carboxylate

The procedure is as in Example 63.

EXAMPLE 150

3-[2-(Benzoylamino)ethyl]-1-benzofuran-5-carboxamide

The procedure is as in Example 67.

EXAMPLE 151

Methyl 8-[2-(3-butenoylamino)ethyl]-2-naphthyl-carbamate

The procedure is as in Examples 74 and 75.

EXAMPLE 152

N-{8-[2-(Acetylamino)ethyl]-2-naphthyl}-4-fluorobenzamide

The procedure is as in Example 1, starting from the compound obtained in Preparation 117.

EXAMPLE 153

Ethyl 3-[2-(benzoylamino)ethyl]-1-benzofuran-5-carboxylate

The procedure is as in Example 62.

PHARMACOLOGICAL STUDY

Example A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

Example B

Melatonin Receptor Binding Study on Pars Tuberalis Cells of Sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 1–4, 1989).

Protocol

1) Sheep pars tuberalis membranes are prepared and used as target tissue in saturation experiments to determine the binding capacities and affinities for 2-[$^{125}$I]-iodomelatonin.
2) Sheep pars tuberalis membranes are used as target tissue in competitive binding experiments using the various test compounds in comparison with melatonin.

Each experiment is carried out in triplicate and a range of different concentrations is tested for each compound. The results enable the determination, after statistical processing, of the binding affinities of the compound tested.

Results

The compounds of the invention appear to have a strong affinity for melatonin receptors.

Example C

1. Melatonin $mt_1$ and $MT_2$ Receptor Binding Study

The $mt_1$ or $MT_2$ receptor binding experiments are carried out using 2-[$^{125}$I]-melatonin as reference radioligand. The radioactivity retained is determined using a liquid scintillation counter.

Competitive binding experiments are then carried out in triplicate using the various test compounds. A range of different concentrations is tested for each compound. The results enable the binding affinities of the compounds tested ($IC_{50}$) to be determined.

2. Study of Binding to $MT_3$ Melatonin Binding Sites

The $MT_3$ site binding experiments are carried out on hamster brain membranes using 2-[$^{125}$I]-melatonin as reference radioligand. The membranes are incubated for 30 minutes with the 2-[$^{125}$I]-melatonin at a temperature of 4° C. and at different concentrations of the test compounds. After incubation, the membranes are quickly filtered and then washed with cold buffer using a filtration system. The radioactivity fixed is measured using a scintillation counter. The $IC_{50}$ values (concentration inhibiting specific binding by 50%) are calculated from competition curves according to a non-linear regression model.

The $IC_{50}$ values found for the compounds of the invention demonstrate binding to one or other of the receptor subtypes, the values being <10 $\mu$M.

Example D

Action of the Compounds of the Invention on the Circadian Rhythms of Locomotive Activity of the Rat The involvement of melatonin in influencing, by day/night alternation, the majority of physiological, biochemical and behavioural circadian rhythms has made it possible to establish a pharmacological model for research into melatoninergic ligands.

The effects of the molecules are tested on numerous parameters and, in particular, on the circadian rhythms of locomotive activity, which are a reliable indicator of the endogenous circadian clock.

In this study, the effects of such molecules on a particular experimental model, namely the rat placed in temporal isolation (permanent darkness), is evaluated.

Experimental Protocol

One-month-old male rats are subjected, as soon as they arrive at the laboratory, to a light cycle of 12 hours' light per 24 hours (LD 12:12). After 2 to 3 weeks' adaptation, they are placed in cages fitted with a wheel connected to a recording system, in order to detect the phases of locomotive activity and thus monitor the nychthemeral rhythms (LD) or circadian rhythms (DD).

As soon as the rhythms recorded show a stable pattern during the light cycle LD 12:12, the rats are placed in permanent darkness (DD).

Two to three weeks later, when the free course (rhythm reflecting that of the endogenous clock) is clearly established, the rats are given a daily administration of the molecule to be tested.

The observations are made by means of visualisation of the rhythms of activity:
- influence on the rhythms of activity by the light/dark cycle,
- disappearance of the influence on the rhythms in permanent darkness,
- influence on the activity by the daily administration of the molecule; transitory or durable effect.

A software package makes it possible:
- to measure the duration and intensity of the activity, the period of the rhythm of the animals during free course and during treatment, possibly to demonstrate by spectral analysis the existence of circadian and non-circadian (for example ultradian) components.

Results

The compounds of the invention clearly appear to allow powerful action on the circadian rhythm via the melatoninergic system.

Example E

Light/dark Cages Test

The compounds of the invention are tested on a behavioural model, the light/dark cages test, which allows the anxiolytic activity of the compounds to be demonstrated.

The apparatus consists of two polyvinyl boxes covered with Plexiglass. One of the boxes is in darkness. A lamp is placed above the other box, yielding a light intensity of approximately 4000 lux in the centre of the box. An opaque plastic tunnel separates the light box from the dark box. The animals are tested individually for a session of 5 minutes. The floor of each box is cleaned between each session. At the start of each test, the mouse is placed in the tunnel, facing the dark box. The time spent by the mouse in the illuminated box and the number of passages through the tunnel are recorded after the first entry into the dark box.

After administration of the compounds 30 minutes before the start of the test, the compounds of the invention significantly increase the time spent in the illuminated cage and the number of passages through the tunnel, which demonstrates the anxiolytic activity of the compounds of the invention.

Example F

Activity of Compounds of the Invention on the Caudal Artery of the Rat

The compounds of the invention were tested in vitro on the caudal artery of the rat. Melatoninergic receptors are present in those vessels, thus providing a relevant pharmacological model for studying melatoninergic ligand activity. The stimulation of the receptors can cause either vasoconstriction or dilation depending on the arterial segment studied.

Protocol

One-month old rats are accustomed to a light/dark cycle of 12h/12h during a period of 2 to 3 weeks. After sacrifice, the caudal artery is isolated and maintained in a highly oxygenated medium. The arteries are then cannulated at both ends, suspended vertically in an organ chamber in a suitable medium and perfused via their proximal end. The pressure changes in the perfusion flow enable evaluation of the vasoconstrictive or vasodilatory effect of the compounds. The activity of the compounds is evaluated on segments that have been pre-contracted by phenylephrine (1 μM). A concentration/response curve is determined non-cumulatively by the addition of a concentration of the test compound to the pre-contracted segment. When the observed effect reaches equilibrium, the medium is changed and the preparation is left for 20 minutes before the addition of the same concentration of phenylephrine and a further concentration of the test compound.

Results

The compounds of the invention significantly modify the diameter of caudal arteries pre-constricted by phenylephrine.

Example G

Pharmaceutical Composition: Tablets

| | |
|---|---|
| 1000 tablets each comprising 5 mg of methyl 3-{2-[(cyclopropylcarbonyl)-amino]ethyl}-1-benzofuran-5-yl-carbamate (Example 75) | 5 g |
| wheat starch | 20 g |
| maize starch | 20 g |
| lactose | 30 g |
| magnesium stearate | 2 g |
| silica | 1 g |
| hydroxypropyl cellulose | 2 g |

We claim:
1. A compound of formula (I):

wherein:
A represents:
a ring system of formula (II):

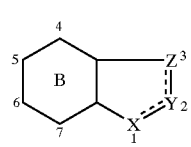

wherein
X represents oxygen, sulphur or nitrogen or $NR_0$ (wherein $R_0$ represents hydrogen, linear or branched $(C_1-C_6)$alkyl, aryl, aryl-$(C_1-C_6)$alkyl in which the alkyl moiety is linear or branched or $SO_2Ph$),
Y represents $C(H)_q$ (wherein q is 0, 1 or 2),
Z represents $C(H)_q$ (wherein q is 0, 1 or 2),
B represents a benzene nucleus,
the symbol ... means that the bonds may be single or double, it being understood that the valency of the atoms is respected,
wherein R substitutes the ring B and R' substitutes the ring XYZ in the 3-position, it being understood that the ring systems of formulae (II) may be unsubstituted or substituted (in addition to the substituents R and R') in the 2-position by one radical selected from $R_a$, $OR_a$, $OCOR_a$, $OSO_2CF_3$ and halogen,
wherein $R_a$ represents hydrogen, unsubstituted or substituted linear or branched $(C_1-C_6)$alkyl, unsubstituted or substituted linear or branched $(C_2-C_6)$alkenyl, unsubstituted or substituted linear or branched $(C_2-C_6)$alkynyl, linear or branched $(C_1-C_6)$polyhaloalkyl, unsubstituted or substituted $(C_3-C_8)$cycloalkyl, unsubstituted or substituted $(C_3-C_8)$cycloalkyl-$(C_1-C_6)$alkyl in which the alkyl group is linear or branched, unsubstituted or substituted $(C_3-C_8)$cycloalkenyl, unsubstituted or substituted $(C_3-C_8)$cycloalkenyl-$(C_1-C_6)$alkyl in which the alkyl group is linear or branched, aryl, aryl-$(C_1-C_6)$alkyl in which the alkyl moiety is linear or branched, aryl-$(C_1-C_6)$alkenyl in which the alkenyl moiety is linear or branched, heteroaryl, heteroaryl-$(C_1-C_6)$alkyl in which the alkyl moiety is linear or branched, heteroaryl-$(C_1-C_6)$alkenyl in which the alkenyl moiety is linear or branched, unsubstituted or substituted linear or branched $(C_1-C_6)$ heterocycloalkyl, unsubstituted or substituted heterocycloalkenyl, substituted or unsubstituted heterocycloalkyl-$(C_1-C_6)$alkyl in which the alkyl moiety is linear or branched, or substituted or unsubstituted heterocycloalkenyl-$(C_1-C_6)$alkyl in which the alkyl moiety is linear or branched, R represents:

a group of formula (V):

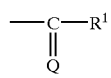

(V)

wherein

Q represents sulphur or oxygen, $R^1$ represents $NR'_a R''_a$ or $OR^1_a$ (wherein $R'_a$ and $R''_a$, which may be the same or different, may take any of the values of $R_a$ and may also form, together with the nitrogen atom carrying them, a 5- to 10-membered cyclic group which may contain, in addition to the nitrogen atom by which it is linked, from one to three hetero atoms selected from oxygen, sulphur and nitrogen, and $R^1_a$ may take any of the values of $R_a$ except for the hydrogen atom), a group of formula (VI):

(VI)

wherein $R^2$ represents $R_a$ as defined hereinbefore, $R^3$ represents $COR'_a$, $CSR'_a$, $CONR'_a R''_a$, $CSNR'_a R''_a$, $COOR'_a$, $CSOR'_a$ or $S(O)_v R'_a$, wherein $R'_a$ and $R''_a$, which may be the same or different, are as defined hereinbefore and may also form, together with the nitrogen atom carrying them, a cyclic group as defined hereinbefore, and v is 1 or 2, a group of formula (VII):

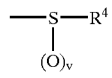

(VII)

wherein v is as defined hereinbefore and $R^4$ represents $NR'_a R''_a$, $NR_a COR'_a$, $NR_a CSR'_a$, $NR_a CONR'_a R''_a$, $NR_a CSNR'_a R''_a$ or $NR_a COOR'_a$, wherein $R_a$, $R'_a$ and $R''_a$ are as defined hereinbefore, or, when A represents a ring system of formula (II) or (III) or biphenyl, forms, together with two adjacent carbon atoms of the cyclic structure A carrying it, a ring of formula (VIII):

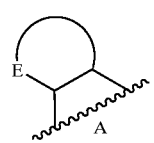

(VIII)

wherein E represents

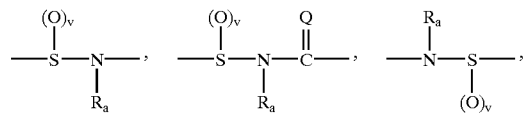

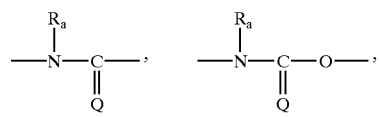

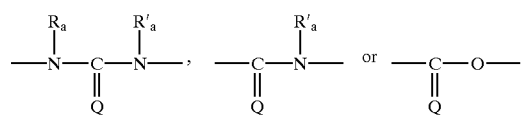

wherein r, Q, $R_a$, $R'_a$ and v are as defined hereinbefore, the ring formed containing from 5 to 7 atoms and it being possible for the ring to contain from 1 to 3 hetero atoms selected from nitrogen, sulphur and oxygen, and one or more unsaturations, and being optionally substituted by one or more radicals, which may be the same or different, selected from $R_a$, $OR_a$, $COR_a$, $COOR_a$, $OCOR_a$, $NR'_a R''_a$, $NR_a COR'_a$, $CONR'_a R''_a$, cyano, oxo, $SR_a$, $S(O)_r R_a$, $SO_2 R_a$, $CSR_a$, $NR_a CSR'_a$, $CSNR'_a R''_a$, $NR_a CONR'_a R''_a$, $NR_a CSNR'_a R''_a$ and halogen, wherein $R_a$, $R'_a$ and $R''_a$, which may be the same or different, are as defined hereinbefore and $R'_a$ and $R''_a$ may also form, together with the nitrogen atom carrying them, a cyclic group as defined hereinbefore, and R' represents a group of formula (IX):

(IX)

wherein

G represents an alkylene chain $-(CH_2)_t-$ (wherein t is an integer such that $1 \leq t \leq 4$), optionally substituted by one or more radicals, which may be the same or different, selected from $R_a$, $OR_a$, $COOR_a$, $COR_a$ (in which $R_a$ is as defined hereinbefore) or halogen, and $R^5$ represents

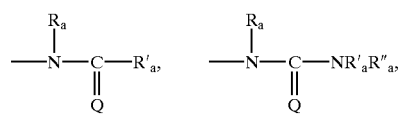

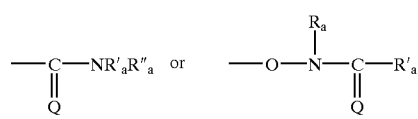

wherein Q, $R_a$, $R'_a$ and $R''_a$ (which may be the same or different) are as defined hereinbefore, it being possible for $R'_a$ and $R''_a$ to form, together with the nitrogen atom carrying them, a cyclic group as defined hereinbefore, it being understood that:

"heterocycloalkyl" is taken to mean any saturated mono- or poly-cyclic group containing from 5 to 10 atoms containing from 1 to 3 hetero atoms selected from nitrogen, oxygen and sulphur, "heterocycloalkenyl" is taken to mean any non-aromatic mono- or poly-cyclic group containing one or more unsaturations, containing from 5 to 10 atoms and which may contain from 1 to 3 hetero atoms selected from nitrogen, oxygen and sulphur, the term "substituted" used in respect of the expressions "alkyl", "alkenyl" and "alkynyl" indicates that the groups in question are substituted by one or more radicals, which may be the same or different, selected from hydroxy, linear or branched ($C_1$–$C_6$)alkoxy, linear or branched ($C_1$–$C_6$)alkyl, linear or branched ($C_1$–$C_6$) polyhaloalkyl, amino and halogen, the term "substituted" used in respect of the expressions "cycloalkyl", "cycloalkylalkyl", "cycloalkenyl", "cycloalkenylalkyl", "heterocycloalkyl", "heterocycloalkenyl", "heterocycloalkylalkyl" and "heterocycloalkenylalkyl" indicates that the cyclic moiety of the groups in question is substituted by one or more radicals, which may be the same or different, selected from hydroxy, linear or branched ($C_1$–$C_6$) alkoxy, linear or branched ($C_1$–$C_6$)alkyl, linear or branched ($C_1$–$C_6$)polyhaloalkyl, amino and halogen, "aryl" is taken to mean any aromatic, mono- or poly-cyclic group containing from 6 to 22 carbon atoms, and also biphenyl, "heteroaryl" is taken to mean any aromatic mono- or poly-cyclic group containing from 5 to 10 atoms containing from 1 to 3 hetero atoms selected from nitrogen, oxygen and sulphur, it being possible for the "aryl" and "heteroaryl" groups to be substituted by one or more radicals, which may be the same or different, selected from hydroxy, linear or branched ($C_1$–$C_6$)alkoxy, linear or branched ($C_1$–$C_6$) alkyl, linear or branched ($C_1$–$C_6$)polyhaloalkyl, cyano, carboxy, nitro, amino and halogen, it being understood that:

when A represents indole, there cannot be any substituents in the 2-position, when A represents indole and R represents —$NHCOR'_a$, —$NHCOOR'_a$ or $NHCONR'_aR''_a$, then G—$R^5$ cannot represent —$(CH_2)_2$—$NHCOR_b$ wherein $R_b$ represents ($C_1$–$C_4$)alkyl or $CF_3$, when A represents benzofuran or benzothiophene, there cannot be any COPh (wherein Ph is substituted or unsubstituted) in the 2-position, when A represents benzofuran or benzothiophene, R cannot represent —$NR_aCOR_c$, —$NHSO_2R_c$, —$NHCOCH_2R_c$ or $NHCONHR_c$ wherein $R_c$ represents heterocyclic or aryl the compound of formula (I) cannot represent:

N-(2-{5-[(4-ethoxyanilino)sulphonyl]-1H-indol-3-yl}ethyl)acetamide, its enantiomers and diastereoisomers, and addition salts thereof with a pharmaceutically acceptable acid or base.

2. A compound of claim 1, wherein A represents a ring system of formula (II) substituted in the 5-position by R as defined in claim 1 and in the 3-position by R' as defined in claim 1.

3. A compound of claim 1, wherein R represents a group of formula (V).

4. A compound of claim 1, wherein R represents a group of formula (VI).

5. A compound of claim 1, wherein R represents a group of formula (VII).

6. A compound of claim 1, wherein R represents a group of formula (V) wherein Q represents oxygen and $R^1$ represents $NR'_aR''_a$ as defined in claim 1.

7. A compound of claim 1, wherein R represents a group of formula (V) wherein Q represents oxygen and $R^1$ represents $OR^1_a$ as defined in claim 1.

8. A compound of claim 1, wherein R represents a group of formula (VI) wherein $R^3$ represents $COR'_a$ wherein $R'_a$ is as defined in claim 1.

9. A compound of claim 1, wherein R represents a group of formula (VI) wherein $R^3$ represents $COOR'_a$ wherein $R'_a$ is as defined in claim 1.

10. A compound of claim 1, wherein R represents a group of formula (VII) wherein v is 2 and $R^4$ represents $NR'_aNR''_a$.

11. A compound of claim 1, wherein R' represents G—$R^5$ wherein G represents an unsubstituted or substituted alkylene chain —$(CH_2)_t$— wherein t is 2 or 3 and $R^5$ represents

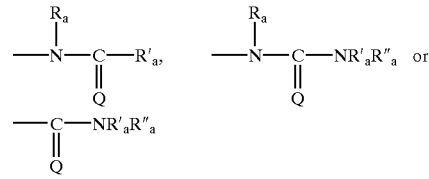

wherein $R_a$, $R'_a$, $R''_a$ and Q are as defined in claim 1.

12. A compound of claim 1, wherein R' represents G—$R^5$ wherein G represents an alkylene chain —$(CH_2)_t$— wherein t is 2 or 3 and $R^5$ represents —$NHCOR'_a$ or —$CONHR'_a$ wherein $R'_a$ is as defined in claim 1.

13. A compound of claim 1, wherein A represents a ring system of formula (II') and R represents a group of formula (V).

14. A compound of claim 1, wherein A represents a ring system of formula (II') and R represents a group of formula (VI).

15. A compound of claim 1, wherein A represents a ring system of formula (II) substituted in the 5-position by a group of formula (V) and in the 3-position by a group of formula (IX).

16. A compound of claim 1, wherein A represents a ring system of formula (II) substituted in the 5-position by a group of formula (VI) and in the 3-position by a group of formula (IX).

17. A compound of claim 1, wherein A represents a ring system of formula (II) substituted in the 5-position by a group of formula (VII) and in the 3-position by a group of formula (IX).

18. A compound of claim 1, wherein A represents a ring system of formula (II), which is substituted in the 5-position by —$CONR'_aR''_a$ wherein $R'_a$ and $R''_a$ are as defined in claim 1 and substituted in the 3-position by a group of formula (IX) wherein G represents an unsubstituted or substituted chain —$(CH_2)_t$—, wherein t is 2 or 3, and $R^5$ represents

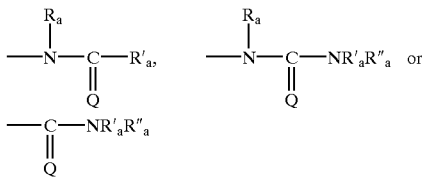

wherein Q, $R_a$, $R'_a$ and $R''_a$ are as defined in claim 1.

19. A compound of claim 1, wherein A represents a ring system of formula (II), which is substituted in the 5-position by —$SO_2NR'_aR''_a$ wherein $R'_a$ and $R''_a$ are as defined in claim 1 and substituted in the 3-position by a group of formula (IX) wherein G represents an unsubstituted or substituted chain —$(CH_2)_t$—, wherein t is 2 or 3, and $R^5$ represents

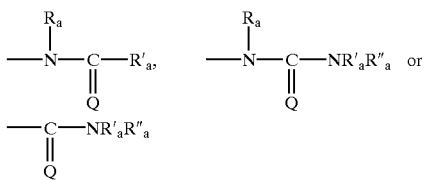

wherein Q, $R_a$, $R'_a$ and $R''_a$ are as defined in claim 1.

20. A compound of claim 1, wherein A represents a ring system of formula (II), which is substituted in the 5-position by —$NHCOR'_a$ wherein $R'_a$ is as defined in claim 1 and substituted in the 3-position by a group of formula (IX) wherein G represents an unsubstituted or substituted chain —$(CH_2)_t$—, wherein t is 2 or 3, and $R^5$ represents

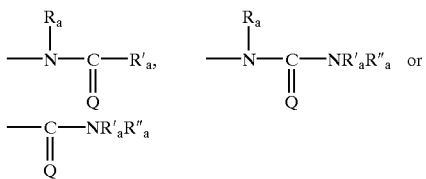

wherein Q, $R_a$, $R'_a$ and $R''_a$ are as defined in claim 1.

21. A compound of claim 1, wherein A represents a ring system of formula (II), which is substituted in the 5-position by —$NHCOOR'_a$ wherein $R'_a$ is as defined in claim 1 and substituted in the 3-position by a group of formula (IX) wherein G represents an unsubstituted or substituted chain —$(CH_2)_t$—, wherein t is 2 or 3, and $R^5$ represents

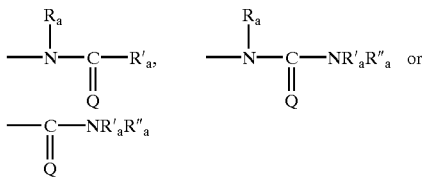

wherein Q, $R_a$, $R'_a$ and $R''_a$ are as defined in claim 1.

22. A compound of claim 1, wherein A represents a ring system of formula (II), which is substituted in the 5-position by —$COOR'_a$ wherein $R'_a$ is as defined in claim 1 and substituted in the 3-position by a group of formula (IX) wherein G represents an unsubstituted or substituted chain —$(CH_2)_t$—, wherein t is 2 or 3, and $R^5$ represents

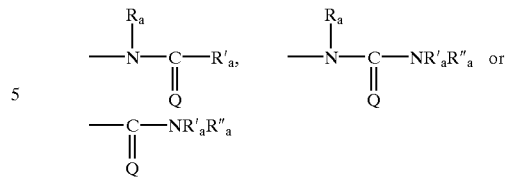

wherein Q, $R_a$, $R'_a$ and $R''_a$ are as defined in claim 1.

23. A compound of claim 1, wherein A represents benzofuran or dihydrobenzofuran, which is optionally substituted (in addition to the substituents R and R').

24. A compound of claim 1, wherein A represents benzothiophene or dihydrobenzothiophene, which is optionally substituted (in addition to the sustituents R and R').

25. A compound of claim 1, wherein A represents indole or indolene, which is optionally substituted (in addition to the substituents R and R').

26. A compound of claim 1, wherein A represents benzofuran or dihydrobenzofuran, which is substituted in the 5-position by R, wherein R is defined as —$NHCOR_a$, $SO_2NHR_a$, $COOR^1_a$ or $CONHR_a$ and wherein $R_a$ and $R^1_a$ are as defined in claim 1, and which is substituted in the 3-position by R', wherein R' is defined as —$(CH_2)_t$—$NHCOR'_a$ or —$(CH_2)_t$—$CONHR'_a$, and wherein t is 2 or 3 and $R'_a$ is as defined in claim 1, and which is optionally substituted (in addition to those R and R' substituents) in the 2-position with substituents selected from $R_a$, $OR_a$, $OCOR_a$, $OSO_2CF_3$ and halogen, as defined in claim 1.

27. A compound of claim 1, wherein A represents benzothiophene or dihydrobenzothiophene, which is substituted in the 5-position by R, wherein R is defined as —$NHCOR_a$, $SO_2NHR_a$, $COOR^1_a$ or $CONHR_a$ and wherein $R_a$ and $R^1_a$ are as defined in claim 1, and which is substituted in the 3-position by R', wherein R' is defined as —$(CH_2)_t$—$NHCOR'_a$ or —$(CH_2)_t$—$CONHR'_a$, and wherein t is 2 or 3 and $R'_a$ is as defined in claim 1, and which is optionally substituted (in addition to those R and R' substituents) in the 2-position with substituents selected from $R_a$, $OR_a$, $OCOR_a$, $OSO_2CF_3$ and halogen, as defined in claim 1.

28. A compound of claim 1, wherein A represents indole or indoline, which is substituted in the 5-position by R, wherein R is defined as —$NHCOR_a$, $SO_2NHR_a$, $COOR^1_a$ or $CONHR_a$ and wherein $R_a$ and $R^1_a$ are as defined in claim 1, and which is substituted in the 3-position by R', wherein R' is defined as —$(CH_2)_t$—$NHCOR'_a$ or —$(CH_2)_t$—$CONHR'_a$, wherein t is 2 or 3 and $R'_a$ is as defined in claim 1, and which is optionally substituted (in addition to those R and R' substituents) in the 2-position with substituents selected from $R_a$, $OR_a$, $OCOR_a$, $OSO_2CF_3$ and halogen, as defined in claim 1.

29. A compound of claim 1, wherein A represents benzofuran or dihydrobenzofuran, which is substituted in the 5-position by R, wherein R is defined as —$NHCOOR_a$ or —$N(Alk)COOR_a$ and wherein $R_a$ is as defined in claim 1 and alk represents alkyl, and which is substituted in the 3-position by R', wherein R' is defined as —$(CH_2)_t$—$NHCOR'_a$ or —$(CH_2)_t$—$CONHR'_a$, wherein t is 2 or 3 and $R'_a$ is as defined in claim 1, and which is optionally substituted (in addition to those R and R' substituents) in the 2-position with substituents selected from $R_a$, $OR_a$, $OCOR_a$, $OSO_2CF_3$ and halogen, as defined in claim 1.

30. A compound of claim 1, wherein A represents benzothiophene or dihydrobenzothiophene, which is substituted in the 5-position by R, wherein R is defined as —$NHCOOR_a$ or —$N(alk)COOR_a$, and wherein $R_a$ is as defined in claim 1 and alk represents alkyl, and which is substituted in the 3-position by R', wherein R' is defined as —(CH$_2$)$_t$—NHCOR'$_a$ or —(CH$_2$)$_t$—CONHR'$_a$, wherein t is 2 or 3 and R'$_a$ is as defined in claim 1, and which is optionally substituted (in addition to those R and R' substituents) in the 2-position with substituents selected from R$_a$, OR$_a$, OCOR$_a$, OSO$_2$CF$_3$ and halogen, as defined in claim 1.

31. A compound of claim 1, wherein A represents indole or indoline, which is substituted in the 5-position by R, wherein R is defined as —NHCOOR$_a$ or —N(alk)COOR$_a$, and wherein R$_a$ is as defined in claim 1 and alk represents alkyl, and which is substituted in the 3-position by R', wherein R' is defined as —(CH$_2$)$_t$—NHCOR'$_a$ or —(CH$_2$)$_t$—CONHR'$_a$, wherein t is 2 or 3 and R'$_a$ is as defined in claim 1, and which is optionally substituted (in addition to those R and R' substituents) in the 2-position with substituents selected from R$_a$, OR$_a$, OCOR$_a$, OSO$_2$CF$_3$ and halogen, as defined in claim 1.

32. A compound of claim 1 selected from:
methyl 3-[2-(2-furoylamino)ethyl]-1-benzofuran-5-carboxylate,
methyl 3-{2-[(cyclopentylcarbonyl)amino]ethyl}-1-benzofuran-5-carboxylate,
methyl 3-{2-[(cyclopropylcarbonyl)amino]ethyl}-1-benzofuran-5-carboxylate,
methyl 3-[2-(3-butenoylamino)ethyl]-1-benzofuran-5-carboxylate,
methyl 3-[2-(benzoylamino)ethyl]-1-benzofuran-5-carboxylate, and
methyl 3-[2-(isobutylamino)ethyl]-1-benzofuran-5-carboxylate,
their enantiomers and diastereoisomers, and addition salts thereof with a pharmaceutically acceptable acid or base.

33. A compound of claim 1 selected from:
N,N-diphenyl-3-[3-(acetylamino)propyl]benzo[b]furan-5-carboxamide,
3-[2-(acetylamino)ethyl]-1-benzofuran-5-carboxamide,
3-{2-[(cyclopropylcarbonylamino]ethyl}-1-benzofuran-5-carboxamide,
3-[2-(2-furoylamino)ethyl]-1-benzofuran-5-carboxamide,
3-{2-[(cyclopropylcarbonyl)amino]ethyl}-N-methyl-1-benzofuran-5-carboxamide,
3-[2-(acetylamino)ethyl]-N-methyl-1-benzofuran-5-carboxamide,
3-{2-[(cyclopentylcarbonyl)amino]ethyl}-N-methyl-1-benzofuran-5-carboxamide,
3-[2-(benzoylamino)ethyl]-N-methyl-1-benzofuran-5-carboxamide,
3-{2-[(cyclopropylcarbonyl)amino]ethyl}-N-ethyl-1-benzofuran-5-carboxamide,
3-[2-(benzoylamino)ethyl]-N-ethyl-1-benzofuran-5-carboxamide,
N-isopropyl-N-2-propynyl)-3-[(acetylamino)methyl]-2-benzylbenzo[b]thiophene-5-carboxamide, and
3-[2-(benzoylamino)ethyl]-1-benzofuran-5-carboxamide.

34. A compound of claim 1 selected from:
N-{3-[2-(acetylamino)ethyl]-1-benzofuran-5-yl}-2,2,2-trifluoroacetamide,
N-{2-[5-(acetylamino)-1-benzofuran-3-yl]ethyl}cyclopropanecarboxamide,
N-{2-[5-(acetylamino)-1-benzothiophen-3-yl]ethyl}-benzamide, and
their enantiomers and diastereoisomers, and addition salts thereof with a pharmaceutically acceptable acid or base.

35. A compound of claim 1 selected from:
N-(3-{5-[(methylamino)sulphonyl]-1-benzofuran-3-yl}propyl)acetamide,
N-(2-{5-[(propylamino)sulphonyl]-1-benzofuran-3-yl}ethyl)acetamide,
N-(2-{5-[(cyclopropylamino)sulphonyl]-1-benzofuran-3-yl}ethyl)benzamide,
N-(2-{5-[(methylamino)sulphonyl]-1-benzofuran-3-yl}ethyl)-2-furamide,
N-(2-{5-[(methylamino)sulphonyl]-1-benzofuran-3-yl}ethyl)cyclopropanecarboxamide,
N-(2-{2-benzyl-5-[(methylamino)sulphonyl]-1-benzothiophene-3-yl}ethyl)acetamide, and
N-(2-{5-[(isopropylamino)sulphonyl]-1-benzofuran-3-yl}ethyl)cyclopropanecarboxamide.

36. A compound of claim 1 selected from:
methyl N-{3-[2-(acetylamino)ethyl]benzo[b]furan-5-yl}carbamate,
methyl 3-{2-[(cyclopropylcarbonyl)amino]ethyl}-1-benzofuran-5-yl-carbamate,
tert-butyl 3-[2-(acetylamino)ethyl]-1-benzofuran-5-yl-carbamate,
tert-butyl 3-[2-(acetylamino)ethyl]-1-benzofuran-5-yl-(methyl)carbamate,
methyl 3-[2-(benzoylamino)ethyl]-1-benzofuran-5-yl-carbamate,
methyl 3-[2-(isobutyrylamino)ethyl]-1-benzofuran-5-yl-carbamate,
methyl 3-[2-(2-furoylamino)ethyl]-1-benzofuran-5-yl-carbamate, and
methyl 3-{2-[(cyclopentylcarbonyl)amino]ethyl}-1-benzofuran-5-yl-carbamate,
their enantiomers and diastereoisomers, and addition salts thereof with a pharmaceutically acceptable acid or base.

37. A method for treating a living animal body afflicted with disorders of the melatoninergic system which are selected from stress, sleep disorders, anxiety, seasonal affective disorder, cardiovascular pathologies, pathologies of the digestive system, insomnia and fatigue resulting form jet lag, schizophrenia, panic attacks, melancholia, depression, appetite disorders, obesity, insomnia, psychotic disorders, epilepsy, diabetes, Parkinson's disease, senile dementia, various disorders associated with normal or pathological ageing, migraine, memory loss Alzheimer's disease, cerebral circulation disorders, sexual dysfunction, and cancers, comprising the step of administering to the living animal body an amount of a compound of claim 1 which is effective for the alleviation of said disorder.

38. A pharmaceutical composition useful for treating melatoninergic disorders which are selected from stress, sleep disorders, anxiety, seasonal affective disorder, cardiovascular pathologies, pathologies of the digestive system, insomnia and fatigue resulting from jet lag, schizophrenia, panic attacks, melancholia, depression, appetite disorders, obesity, insomnia, psychotic disorders associated with normal or pathological ageing, migraine, memory loss Alzheimer's disease, cerebral circulation disorders, sexual dysfunction, and cancers, comprising, as active principle an affective amount of a compound as claimed in claim 1, together with one or more pharmaceutically-acceptable excipients or vehicles.

39. A compound of claim 1, wherein A represents benzofuran or dihydrobenzofuran, which is optionally substituted (in addition to the substituents R and R') in the 2-position.

40. A compound of claim 1, wherein A represents benzothiophene or dihydrobenzotiophene, which is optionally substituted (in addition to the substituents R and R') in the 2-position.

41. A compound of claim 1, wherein A represents indole or indolene, which is optionally substituted (in addition to the substituents R and R') in the 2-position.

* * * * *

UNITED STATES PATENT AND TRADEMARK OFFICE
CERTIFICATE OF CORRECTION

PATENT NO. : 6,605,632 B1  
DATED : August 12, 2003  
INVENTOR(S) : Daniel Lesieur et al.

It is certified that error appears in the above-identified patent and that said Letters Patent is hereby corrected as shown below:

<u>Column 60,</u>  
Line 44, "XYZ" should be -- containing X, Y and Z --.

<u>Column 67,</u>  
Line 36, "cyclopropylcarbonylamino" should be -- cyclopropylcarbonyl)amino --.  
Line 51, "N-2-propynyl)" should be -- N(2-propynyl) --.

<u>Column 68,</u>  
Line 49, please insert the following after "psychotic disorders" "epilepsy, diabetes, Parkinson's disease, senile dementia, various disorders --.

Signed and Sealed this

Sixteenth Day of March, 2004

JON W. DUDAS  
*Acting Director of the United States Patent and Trademark Office*